US008999167B2

(12) United States Patent
Nakano et al.

(10) Patent No.: US 8,999,167 B2
(45) Date of Patent: Apr. 7, 2015

(54) COMPOSITE POROUS MEMBRANE AND PROCESS FOR PRODUCING THE SAME

(75) Inventors: Yasuhiro Nakano, Yokohama (JP); Naoko Ishihara, Kawasaki (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 1175 days.

(21) Appl. No.: 10/567,022

(22) PCT Filed: Aug. 4, 2004

(86) PCT No.: PCT/JP2004/011165
§ 371 (c)(1),
(2), (4) Date: Jul. 14, 2006

(87) PCT Pub. No.: WO2005/014149
PCT Pub. Date: Feb. 17, 2005

(65) Prior Publication Data
US 2007/0029256 A1 Feb. 8, 2007

(30) Foreign Application Priority Data

Aug. 7, 2003 (JP) ................................. 2003-288882
Oct. 20, 2003 (JP) ................................. 2003-358980

(51) Int. Cl.
*B01D 61/00* (2006.01)
*B01D 69/02* (2006.01)
*A61M 1/36* (2006.01)

(52) U.S. Cl.
CPC ............ *B01D 69/02* (2013.01); *A61M 1/3633* (2013.01)

(58) Field of Classification Search
CPC ..... A61M 1/3633; B01D 69/02; B01D 69/10; B01D 69/12; C12N 5/0068
USPC ............... 210/641, 490, 500.21, 500.22, 767; 435/297.1, 373; 264/45.1; 427/245; 257/643
See application file for complete search history.

(56) References Cited

U.S. PATENT DOCUMENTS 3,912,834 A 10/1975 Imai et al.
4,673,504 A * 6/1987 Ostreicher et al. ....... 210/500.22
(Continued)

FOREIGN PATENT DOCUMENTS

DE 10058258 8/2002
EP 0462426 12/1991
(Continued)

OTHER PUBLICATIONS

Machine Translation of JP2001-157574, Shimomura et al.*
(Continued)

*Primary Examiner* — Dirk Bass
(74) *Attorney, Agent, or Firm* — Greenblum & Bernstein, P.L.C.

(57) ABSTRACT

There is provided a composite porous membrane comprising a porous membrane comprised of an organic polymeric compound, and a supporting porous membrane adjacent to the porous membrane, characterized in that the organic polymeric compound constituting the porous membrane penetrates in at least part of a surface adjacent to porous membrane of the supporting porous membrane, the porous membrane having specified opening ratio, average pore diameter, standard deviation of pore diameter, ratio of through pore, average membrane thickness, standard deviation of membrane thickness and internal structure, and that the supporting porous membrane has communicating pores of 0.5 D µm or greater average pore diameter. Further, there are provided a blood filtration membrane comprising the composite porous membrane; a leukocyte removing filter unit comprising the composite porous membrane as a second filter; and, utilizing the composite porous membrane, a cell culturing diaphragm and method of cell culturing.

5 Claims, 2 Drawing Sheets

(56) References Cited

U.S. PATENT DOCUMENTS

| | | | |
|---|---|---|---|
| 4,936,998 A | 6/1990 | Nishimura et al. | |
| 5,240,615 A | 8/1993 | Fishman | |
| 5,298,165 A | 3/1994 | Oka et al. | |
| 5,522,991 A * | 6/1996 | Tuccelli et al. | 210/490 |
| 5,665,596 A * | 9/1997 | Mussi | 435/373 |
| 6,280,791 B1 * | 8/2001 | Meyering et al. | 427/244 |
| 6,645,388 B2 * | 11/2003 | Sheikh-Ali | 210/767 |
| 2003/0150808 A1 * | 8/2003 | Morikawa et al. | 210/650 |
| 2006/0097361 A1 * | 5/2006 | Tanaka et al. | 257/643 |

FOREIGN PATENT DOCUMENTS

| | | |
|---|---|---|
| JP | 54-046811 | 4/1979 |
| JP | 56-135525 | 10/1981 |
| JP | 2-180625 | 7/1990 |
| JP | 04-317732 | 11/1992 |
| JP | 5-34337 | 2/1993 |
| JP | 7-204477 | 8/1995 |
| JP | 08-311231 | 11/1996 |
| JP | 10-295369 | 11/1998 |
| JP | 2001-157574 | 6/2001 |
| JP | 2001-252540 | 9/2001 |
| JP | 2003-149096 | 5/2003 |
| JP | 2004-236788 | 8/2004 |
| JP | 2003-80538 | 3/2006 |
| WO | 87/05812 | 10/1987 |
| WO | 9217265 | 10/1992 |
| WO | 03/047655 | 6/2003 |

OTHER PUBLICATIONS

Machine Translation of JP2003-149096, Tanaka et al.*
Polymer Preprints, Japan vol. 50, No. 12 (2001), p. 2804, with a partial English translation.
Polymer Preprints, Japan vol. 51, No. 5 (2002), p. 961, with a partial English translation.
Saishin-igaku vol. 58, No. 1 (2003), p. 63, with a partial English translation.
English Language Abstract of JP 2001-252540.
English Language Abstract of JP 7-204477.
English Language Abstract of JP 2-180625.
English Language Abstract of JP 56-135525.
English Language Abstract of JP 2001-157574.
English Language Abstract of W.I.P.O. 87/05812.
English Language Abstract of JP 5-34337.
English Language Abstract of JP 54-046811.
English Language Abstract of JP 2003-149096.
Machine Translation of JP 2004-236788.
Office Action issued in EP Patent Application No. 04 771 202.1, mailed Oct. 20, 2014.

* cited by examiner

COMPOSITE POROUS MEMBRANE AND PROCESS FOR PRODUCING THE SAME

TECHNICAL FIELD

The present invention relates to a composite porous membrane capable of effectively and efficiently separating target substances of micron size, such as various types of bacteria, yeasts, or cells, which has easy handlability in use and membrane strength sufficient for facilitating the processing thereof into various types of filter forms.

In addition, the present invention also relates to a blood filtration membrane, a process for producing a leukocyte-removed suspension causing only a small loss of hemocyte suspension, and a leukocyte removal filter device, which are used when leukocytes are removed from a hemocyte suspension including, as a representative example, whole blood or a blood product used for blood transfusion.

Moreover, the present invention relates to: a cell culture diaphragm, which efficiently allows two or more types of different cell groups to come into contact with one another, while maintaining a state where such different cell groups are not mixed with one another and are kept separated from one another, when such different cell groups are co-cultured in a culture solution; and a process for culturing cells using a composite porous membrane.

BACKGROUND ART

In a medical field, a bioprocess field, and a regenerative medical field, which use cells, it is important to develop a technique of effectively and efficiently separating such cells. In addition to the centrifugation technique that has conventionally constituted mainstream, the development of a membrane material used for separation directed towards the efficiency of cell separation (reduction in the time required for filtration operations and cost reduction), and the development of a precise cell separation technique using-magnetic beads modified with antibodies, have actively been progressing in recent years. Among others, cell separation using a membrane material is considered to be an efficient cell separation technique, and thus such cell separation technique intends to be widely applied in a medical field and a bioprocess field.

For example, in a pharmaceutical manufacturing field, the development of a bioprocess of producing value-added pharmaceutical products such as erythropoietin, human growth hormone, human insulin or interferon has vigorously been progressing, using animal cells. In addition, in a bioprocess involving a suspended cell culture method for example, various membrane materials are used in a "cell separation process" of separating cells cultured at a large scale in a fermenter from a medium containing useful components, and also in a "purification process" of isolating such useful components from the separated medium. The cost required for such a cell separation process and a purification process in the aforementioned bioprocess makes up a major part in the total pharmaceutical manufacturing cost. Thus, the development of efficient cell separation and purification processes is important. Accordingly, it is strongly desired that a filter structure capable of efficiently avoiding clogging caused by cells, cell-derived components, culture solution-derived components, etc. over the whole process, and a filtration system, be designed.

In the aforementioned process using a filter, namely, in a process ranging from a cell separation process to a process of purifying useful components, in order to suppress clogging as much as possible, so as to improve cost performance regarding pharmaceutical manufacturing, first of all, it is important that cells are separated from a medium effectively (the improvement of a cell concentration rate) and efficiently (reduction in filtration time) at the initial stage. For such purpose, the effectiveness of the use of a suitable pre-filter has been known. Thus, meshes having a pore size suitable for cell separation, high pore size uniformity (a membrane material with high pore size uniformity does not have a small pore size portion that is likely to cause clogging), and high opening ratio, are often used as such pre-filters. Accordingly, it can be said that a filter having a pore size and pore size uniformity necessary for efficiently capturing and separating cells, and high opening ratio that enables rapid filtration, is preferable also in cell separation.

When a filter for separating or removing cells (generally having a size ranging from several microns to several tens of microns) is conceived, if taking into consideration deformation of cells occurring during filtration, a pre-filter having a pore size of several microns, pore size uniformity, and high opening ratio, is mainly preferably used. However, in the case of a polymeric fiber mesh filter that is generally often used as a pre-filter for example, the smallest pore size of such a filter is a square pore with a side of 20 μm or less. Thus, when such a filter is used as a filter for cell separation, cells are dropped out of such pores, and thus it does not function as an effective filter (or pre-filter) in many cases.

On the other hand, some metal mesh filters or polymeric fiber mesh filters produced by special production methods have a pore size of several μm. In such a case, the diameter of such a metal fiber or polymeric filter cannot be extremely decreased, and as a result, the opening ratio thereof is generally significantly reduced. Moreover, since water permeability is low and the clogging of the filter easily takes place, such a metal mesh filter or polymeric fiber mesh filter cannot be an effective filter used for cell separation or elimination.

As a product having a shape that is not that of a mesh filter, an "etched membrane," which is produced by applying electron beam or ion beam to a thin membrane such as polycarbonate and then subjecting to an etching process, has been broadly known. Such an etched membrane has cylindrical pores with a uniform pore size, and the uniformity of such a pore size is extremely high. However, only several % of opening ratio can be obtained due to the production process thereof. (If opening ratio intended to increase, pore size uniformity would be lost.) When such an etched membrane is used as a separation membrane, the membrane thickness thereof must be at the minimum 10 μm for strength retention (in general, a thickness between 15 and 20 μm). However, since the pore length becomes greater than the pore size, filtration resistance increases, and thus it cannot be said that filtration efficiency is sufficient. Moreover, since cylindrical pores produced by such a production method are of straight pore-type, and many of them independently exist, it is extremely rare that pores are connected with one another in a membrane (pores communicate with one another). This is also a factor for low filtration efficiency.

Patent Document 1 discloses a porous polymer membrane wherein micro-porous layer (A) and porous layer (B) having straight pore-type pores exist as a laminated structure. This publication describes that porous layer (A) has mechanical strength and that as a result, the thickness of an etched membrane as porous layer (B) can be reduced, such as one with a thickness of 10 μm or less. However, since the opening ratio, porous structure, and internal membrane structure of porous layer (B) are the same as those of the conventional etched membrane, filtration efficiency is not sufficient. Thus, this porous polymer membrane cannot be an efficient separation filter for cells or the like.

In addition, Patent Document 2 discloses a method for producing a porous membrane with controlled pore size, which comprises applying visible ray or far ultraviolet ray to a polymer membrane via a mask and then eliminating the light irradiation region from the polymer membrane. This publication also discloses a method for forming (integrating) such a porous membrane on (with) a substrate (supporting medium) such as a non-woven fabric or synthetic paper. A porous membrane integrated with a substrate that is obtained by this method has a structure similar to that of the porous polymer membrane disclosed in Patent Document 1. However, since the region in which pores are formed can be controlled with a mask, it becomes possible to set opening ratio at relatively high. Thus, it is anticipated that filtration efficiency is also improved to a certain extent. However, since pores are formed by light irradiation, the pore structure and internal membrane structure thereof are the same as those of an etched membrane. Furthermore, this integration method involves spin-coating a polymer solution on a substrate with a rubber roller, and then drying it, so as to form a porous membrane. Thus, reduction in membrane thickness is difficult, and the polymer solution is likely to penetrate into the supporting medium substrate. As a result, reduction in the thickness of a porous membrane and the uniformity of membrane thickness become difficult, and the structure of a composite membrane is likely to become non-uniform. In particular, this phenomenon significantly takes place when a membrane is formed on a supporting porous substrate having a large average pore size, which has low filtration resistance or on which cells can easily move. Accordingly, a membrane material obtained by this technique cannot either be an efficient separation filter for cells or the like.

That is to say, a filter material having pores with a pore size of several μm (for example, approximately 1 to 5 μm), which has high pore size uniformity and high opening ratio, wherein the pores are short in the direction of a membrane thickness (that is, the membrane thickness is thin), and they are connected with one another in the membrane, and which also has excellent mechanical strength, is useful as an effective and efficient separation filter used for cells or the like (or a pre-filter).

Recently, Non-Patent Documents 1 and 2 have described that a micro droplet of water condensed and generated on a polymer solution due to the loss of latent heat during a solvent volatilization process from the polymer solution acts as a template, and that a honeycomb-structured thin porous membrane having through-pores with a pore diameter of several μm order, which has high pore size uniformity and high opening ratio, can be finally produced using various materials. This thin membrane has almost the same thickness as the diameter of a through-pore, and pores adjacent to each other are connected with each other in the membrane. Thus, this membrane adopts a structure wherein pores communicate with one another in the direction of a membrane flat surface. It is anticipated that a honeycomb-structured thin porous membrane having such a structure be used as an effective and efficient cell separation filter (or pre-filter).

Such a honeycomb-structured thin porous membrane is produced by casting a solution of an organic polymer in a hydrophobic organic solvent on a smooth solid substrate (for example, a glass, silicon wafer, metal plate, polymer solid gel, etc.), blowing air with high humidity of 40% to 95% thereon, so as to form a honeycomb structure on the substrate, and then peeling it off. However, since the strength of the obtained honeycomb-structured thin porous membrane is generally extremely low, the membrane should be peeled from the solid substrate slowly and carefully. Otherwise, the membrane is broken. Accordingly, in many cases, it is necessary that a thin membrane have previously been got wet with ethanol or the like, so as to improve peeling properties. That is to say, since the aforementioned production process using a smooth solid substrate is complicated and has poor production stability, it is naturally predicted that it becomes extremely difficult to achieve a continuous membrane formation process or a membrane formation process for realizing high productivity. In addition, in the case of using a smooth solid substrate, if the affinity of a water droplet acting as a template for the solid substrate is insufficient, a honeycomb-structured thin porous membrane has insufficient formation of through-pore in many cases. If the formation of through-pores is insufficient, it cannot exhibit functions as a filter material.

Patent Document 3 discloses a method for obtaining a honeycomb-structured thin porous membrane, which comprises casting a hydrophobic organic solvent solution on the water surface to form a honeycomb structure, and then skimming this structure with a frame of 5 mmϕ. With regard to such membrane formation using a water substrate, the formation of through-pores tend to be easy. However, since it is difficult to uniformly cast a solution on the water surface, it is difficult to form a membrane with a large area. Moreover, depending on materials, wrinkles are generated due to the contraction of a membrane during a process of removing a solvent. Accordingly, it is predicted that it is extremely difficult also for this method to achieve a process for realizing high productivity.

Furthermore, a honeycomb-structured thin porous membrane material obtained by the aforementioned method has extremely low membrane strength. Thus, when such a membrane material is singly used as a cell separation filter in a bioprocess field or medical field, it is predicted that membrane break takes place at a high frequency. Further, it is also difficult to process such a membrane into a form other than a flat membrane, such as a roll-, pleated-, cylindrical, or bag-form, and to use it. That is to say, such a thin membrane material cannot directly constitute a practical filter material, and thus, it is essential to impart practical mechanical strength to such a membrane material.

A membrane material having pores with a pore diameter of several μm, which has high pore size uniformity, high opening ratio, and a membrane structure extremely excellent in terms of filtration efficiency, and which also has practical mechanical strength, is useful as an effective and efficient separation filter (or pre-filter) used for cells or the like. Such a membrane material is particularly useful for separation of blood cells in a blood filtration field, and more specifically for separation of blood plasma from whole blood or the removal of leukocytes from various blood products.

In recent years, in order to reduce the physical burden of a patient to which transfusion therapy is applied, the importance of a technique of highly removing leukocytes from a hemocyte suspension including, as typical examples, whole blood and a blood product used for transfusion (an erythrocyte product, a thrombocyte product, a blood plasma product, etc.) has increased in a medical field.

An example of a method for removing leukocytes is a filter method, which comprises filtration of a hemocyte suspension, using, as a filter element, a fibrous filter element such as a non-woven fabric, or a porous body having continuous pores in a three-dimensional network state. This filter method is advantageous in that it has high capability of removing leukocytes, in that the operations are simple and easy, and in that it is excellent in terms of cost performance. Thus, at present, the filter method is widely applied in medical sites. A filter used in this method has been known as a "leukocyte removal filter."

Representative examples of such a leukocyte removal filter may include: filters comprising, as a filter element, a non-woven fabric consisting of ultrafine fibers such as polyester, as disclosed in Patent Documents 4 and 5; and filters comprising, as a filter element, a porous body having continuous pores in a three-dimensional network state consisting of polyurethane or the like, as disclosed in Patent Document 6. These publications disclose that the use of such filters achieves 99.99% or more of capability of removing leukocytes.

When a hemocyte suspension is filtrated using a leukocyte removal filter, a portion of the hemocyte suspension remains in a filter element after completion of the filtration. This results in the loss of a precious hemocyte suspension (in particular, in the case of an expensive blood product). Accordingly, in order to improve the cost performance of users dealing with large quantities of blood products, the need for the development of a product, the volume of a filter element of which is reduced, so as to reduce the loss of a hemocyte suspension, while maintaining the ability of a leukocyte removal filter to remove leukocytes (99.99% or more), has significantly increased under present circumstances.

The aforementioned Patent Document 4 discloses a leukocyte removal filter formed by coating the surface of a non-woven fabric used as a filter element with a coating agent containing a nonionic hydrophilic group and a nitrogen-containing basic functional group (for example, a copolymer consisting of 2-hydroxyethyl methacrylate and 2-(diethylamino)ethylmethacrylate, and then laminating a plurality of the thus coated non-woven fabrics. In this case, it is considered that the removal (capturing) of leukocytes is carried out by adsorption mechanism, and that the nitrogen-containing basic functional group has the effect of selectively adsorbing leukocytes and the nonionic hydrophilic group has the effect of suppressing non-selective adsorption of various blood cell components.

In order to reduce the volume of a filter element in such a leukocyte removal filter while maintaining its capability of removing leukocytes, it is considered adequate to increase the content of nitrogen-containing basic functional groups acting as leukocyte-selective affinity functional groups for the purpose of increasing capability of removing leukocytes per unit volume of a coated non-woven fabric. However, as a matter of fact, not only the adsorption ability of leukocytes but also the adsorption ability of other blood cell components (erythrocytes or thrombocytes) is increased by the increase in the quantities of the nitrogen-containing basic functional groups (non-selective adsorption). Consequently, the ability to selectively capture leukocytes is rather decreased. In some serious cases, the clogging of the filter occurs as a result of the adsorption of large quantities of blood cell components. Thus, it cannot be said that an increase in the quantities of nitrogen-containing basic functional groups is effective.

Patent Document 7 discloses a method for removing leukocytes from blood using an etched membrane with a pore size between 3 and 10 μm. In addition, Patent Document 8 describes that the honeycomb-structured thin porous membrane described in Non-Patent Documents 1 and 2 is used as a filter element for filtration of human blood, thereby obtaining excellent ability to selectively remove leukocytes. Interestingly, these results show that using a novel thin porous membrane material having a uniform pore size of several-μm order, depending on size effect, only leukocytes can be selectively captured from among leukocytes (with a diameter of approximately 15 μm), erythrocytes (with a diameter of approximately 7 μm), and thrombocytes (approximately 3 μm) existing in human blood. Such a filter element becomes a focus of attention also as a novel blood cell separation filter material.

However, when such an etched membrane or honeycomb-structured thin porous membrane is used as a filter element for a leukocyte removal filter, such a membrane enables only superficial capturing of leukocytes on the surface of a thin porous membrane. Thus, in order to capture all leukocytes contained in 450 $cm^3$ of human whole blood for example, without the clogging of a filter, a thin porous membrane with an extremely large area is necessary. Consequently, since the size of a filter must be significantly larger than that of the conventional filter, such a filter is problematic in that (1) workability is significantly decreased in medical sites, (2) a filter holder (or filter housing) becomes significantly large, and the production cost is also significantly increased, and (3) in the formation of a thin porous membrane with a large area, product management (mainly, the management of pinholes or pore size uniformity) is extremely difficult in terms of mechanical strength. Thus, it is difficult to say that this is a practical technique.

As stated above, in order to significantly reduce the amount of a hemocyte suspension remaining in a filter element while maintaining the ability of a leukocyte removal filter to remove leukocytes, it is radically necessary to significantly reduce the volume of the filter element. In order to realize such reduction in the volume of filter element, it is essential to develop a leukocyte removal technique of allowing a small filter element to exhibit high capability of removing leukocytes. However, as it has conventionally been studied, it has been difficult to achieve such a technique only by designing the balance of a subtle chemical interaction between each blood cell component and a filter element surface or by optimizing functional groups.

In a medical field and a bioprocess field, in order to achieve a cell culture for allowing various types of useful cells to effectively grow, various techniques regarding the search for a culture solution composition, the design of a scaffolding for effective cell growth, etc., have been developed.

In particular, in recent years, regenerative medicine, in which stem cells having latent ability to differentiate into various types of organs are treated, has become a focus of attention. Regenerative techniques of regenerating several types of organs such as blood vessel, heart muscle, or pancreas, are at a stage in a process of clinical application. For further development of such regenerative medicine, large quantities of stem cells are necessary for conducting various basal and clinical experiments. Thus, at present, in addition to the development of a technique of collecting stem cells from a stem cell source, the development of a technique of allowing the thus collected undifferentiated stem cells to effectively grow in vitro has become a focus of attention.

For example, the effectiveness of regenerative medicine involving transplantation of hematopoietic stem cells has previously been focused in the treatments of acute myelocytic leukemia or anaplastic anemia, including bone marrow transplantation as a typical example. Currently, the effectiveness of regenerative medicine has become a focus of attention also in vascularization therapy for patients with the gravest peripheral arteriosclerosis (Buerger's disease, arteriosclerosis obliterans, diabetic gangrene, etc.). Such a vascularization therapy involving transplantation of hematopoietic stem cells has increasingly recognized by the medical profession. Accordingly, in order to further develop transplantation of hematopoietic stem cells for the treatment of various diseases including the aforementioned diseases in future, it is necessary to develop a technique of ensuring sufficient quantities of hematopoietic stem cells used for studies or clinical application.

At present, representative examples of a source of hematopoietic stem cells may include bone marrow, peripheral blood, and cord blood. From the viewpoint of noninvasiveness to a donor and reduction in hours on duty during collection of hematopoietic stem cells, at current, transplantation of hematopoietic stem cells derived from cord blood has sharply increased. For example, in April, 2003, the number of transplantation of cord blood-derived hematopoietic stem cells per month (47 cases) has exceeded the number of bone marrow transplantation (46 cases) for the first time.

However, collection of hematopoietic stem cells from a cord blood source is disadvantageous in that the amount collected from a single donor is small. Thus, under the current circumstances, cord blood-derived hematopoietic stem cells are mainly transplanted into a child patient whose body is small. Accordingly, if undifferentiated hematopoietic stem cells collected from the cord blood of a single donor were allowed to grow in vitro, the cells could also be naturally transplanted into adult patients. Thus, it can be said that this becomes an extremely revolutionary technique.

That is to say, it is important for hematopoietic stem cell transplantation to collect as many hematopoietic stem cells as possible from a single donor and then transplant them. Thus, studies have been vigorously conducted directed towards the effective growth of not only cord blood-derived hematopoietic stem cells, but also peripheral blood- and bone marrow-derived hematopoietic stem cells.

Recently, it has been reported that when cord blood-derived hematopoietic stem cells are co-cultured with mouse bone marrow-derived stromal cells in the presence of a certain kind of cytokine, the growth of undifferentiated CD34 positive cells is significantly promoted (Non-Patent Document 3). In this case, the cord blood-derived hematopoietic stem cells are co-cultured with the mouse bone marrow-derived stromal cells in a state where the two types of cells are separated from each other with a polymer diaphragm material. This publication describes that the hematopoietic stem cells are allowed to come into contact with villi extended from the stromal cells via the pores of the polymer diaphragm material, so that the above hematopoietic stem cells can effectively grow while they remain undifferentiated. If such a culture technique of co-culturing hematopoietic stem cells with different cells in a state where the two types of cells are separated with a diaphragm material and allowing the hematopoietic stem cells to grow by intracellular contact via the pores of the diaphragm were developed, it would facilitate the separation and collection of the grown hematopoietic stem cells. Accordingly, there is a possibility that such co-culture would constitute an extremely practical in vitro hematopoietic stem cell growth method.

As stated above, in order to allow a certain type of useful cells to grow by co-culture with different cells and then easily and efficiently recover such useful cells after the growth, it is effective to use a diaphragm material having a large number of pores. A diaphragm material used for such purpose is required to have the following properties:
(1) the diaphragm material has as large pores as possible within a range where cells do not move through the diaphragm, so as to effectively conduct only intracellular contact;
(2) in order to conduct effective intracellular contact, the diaphragm has high opening ratio;
(3) in order to conduct effective intracellular contact, the diaphragm has a small membrane thickness;
(4) it has high membrane strength that is sufficient for facilitating an operation to recover useful cells after the growth, or the like; and
(5) it can be processed into various membrane forms suitable for effective cell culture.

In order to satisfy condition (1) above, membrane materials with high pore size uniformity are first selected. Thereafter, from among such membrane materials with a uniform pore size, a membrane material having the largest average pore size within a range where cells do not move through a diaphragm is preferably selected and used.

As described in the section regarding a cell separation or elimination filter, examples of such a membrane material with high pore size uniformity may include a polymeric fiber mesh, a metal mesh, an etched membrane, and a special thin porous membrane formed using a micro water droplet as a template.

A common polymeric fiber mesh has a large pore size. Thus, when such a polymeric fiber mesh is used as a cell culture diaphragm, general cells move through pores. In particular, such a polymeric fiber mesh cannot be used as a diaphragm used for the culture of hematopoietic stem cells having a diameter of approximately 7 μm.

Several metal meshes, or polymeric fiber meshes formed by special production methods, have a pore size of less than 10 μm. However, in general, since such meshes have significantly reduced opening ratio, they do not satisfy condition (2) above. Thus, although such meshes can be used as diaphragms, they do not enable effective intracellular contact. Accordingly, it cannot be said that such meshes are practical as diaphragm used for the co-culture of cells.

An etched membrane is used as a diaphragm in Non-Patent Document 3. However, the opening ratio of such an etched membrane is low, and thus this membrane cannot satisfy the aforementioned condition (2), as in the case of meshes. Thus, this etched membrane cannot be a practical diaphragm for the co-culture of cells. Although the membrane integrated with the supporting medium of Patent Document 2 satisfies condition (2) to a certain extent, but it is still insufficient. Moreover, since a polymer solution is applied on the supporting medium by spin-coating with a rubber roller, it is difficult to form a thin membrane. Further, since the polymer solution is likely to penetrate into the supporting medium substrate, it is also difficult to form a thin porous membrane and uniformize the membrane thickness. Thus, the structure of a composite membrane is likely to become non-uniform. Hence, since it is difficult to obtain a porous membrane as a uniformly thin membrane, such a porous membrane cannot satisfy the aforementioned condition (3). A membrane material produced by this technique cannot either be a diaphragm for efficient cell culture.

A special thin porous membrane produced using a micro water droplet as a template satisfies the aforementioned conditions (1) to (3). Thus, there is a possibility that this membrane can be used as a diaphragm material for efficient cell culture. However, since such a membrane has a membrane thickness of several microns, its strength is extremely low, and thus the membrane is easily broken. Accordingly, it is difficult to use a membrane with a large area for the purpose of culturing large quantities of cells or to process such a membrane into various forms (for example, in the form of a bag, roll, or the like) that are suitable for the growth of large quantities of cells or separation and collection of cells of interest. Therefore, such a membrane cannot satisfy the aforementioned conditions (4) and (5), and thus it cannot directly be a practical cell culture diaphragm.

[Non-Patent Document 1] Polymer Preprints, Japan, Vol. 50, No. 12 (2001), p. 2804
[Non-Patent Document 2] Polymer Preprints, Japan, Vol. 51, No. 5 (2002), p. 961
[Non-Patent Document 3] Saishin Igaku (Latest Medicine), Vol. 58, No. 1 (2003), p. 63
[Patent Document 1] JP-A-2-180625
[Patent Document 2] JP-A-56-135525
[Patent Document 3] JP-A-2001-157574
[Patent Document 4] International Publication WO87/05812
[Patent Document 5] U.S. Pat. No. 5,298,165
[Patent Document 6] JP-A-5-34337
[Patent Document 7] JP-A-54-46811
[Patent Document 8] JP-A-2003-149096

DISCLOSURE OF THE INVENTION

Problems to be Solved by the Invention

It is an object of the present invention to provide a membrane material capable of effectively and efficiently separating target substances of micron size (for example, cultured cells or blood cells) based on precise size separation, which has membrane strength sufficient for easy handlability and enables the processing thereof in various types of membrane forms. In addition, it is another object of the present invention to provide a process for producing a leukocyte-removed hemocyte suspension using the above membrane material, which significantly reduces the volume of a filter element while maintaining high capability of removing leukocytes, and which is able to significantly reduce the loss of a hemocyte suspension after filtration operation, and a leukocyte removal filter device.

Moreover, it is another object of the present invention to provide a process for culturing cells using the above membrane material as a cell culture diaphragm used for the co-culture of two or more types of different cell groups in a cell culture solution, which efficiently allows such two or more types of different cell groups to come into contact with one another, while maintaining a state where such different cell groups are not mixed with one another and are kept separated from one another.

Means for Solving the Problems

As a result of intensive studies directed towards achieving the aforementioned objects, the present inventors have completed the present invention.

With regard to the leukocyte removal filter using a non-woven fabric described in the section regarding prior art techniques, the present inventors have analyzed the relationship between the number of such non-woven fabrics and the capability of removing leukocytes. As a result, the inventors have found that when the number of such non-woven fabrics is small, the capability of removing leukocytes increases as the number of such fabrics increases, but that when the number of non-woven fabrics becomes large, such effects gradually decrease. The inventors have also found that when the composite porous membrane of the present invention, which has pores with a size capable of selectively capturing leukocytes, having a high size uniformity, and which also has practical mechanical strength, is used with the combination of a non-woven fabric or a porous body having continuous pores in a three-dimensional network state under specific conditions, drastic reduction in the volume of a filter element can be realized while maintaining high capability of removing leukocytes, thereby completing the present invention.

That is to say, the present invention includes the following (1) to (14):

(1) A composite porous membrane, which comprises at least one porous membrane comprising an organic polymer and at least one supporting porous membrane adjacent thereto,
wherein the organic polymer constituting the porous membrane penetrates into at least a portion of the surface of the supporting porous membrane adjacent to the porous membrane, and
when the membrane flat surface of the porous membrane is observed using a photomicrograph, the porous membrane has an opening ratio between 10% and 90%, an average pore diameter D (μm) of $0.1 \leq D \leq 50$, a standard deviation σd (μm) of pore diameter of $0.1 \leq \sigma d/D \leq 0.6$, and the percentage of through-pores to all the pores of the porous membrane of 30% or more; when a membrane section thereof is observed using a photomicrograph, the porous membrane has an average membrane thickness T (μm) defined by $0.05 \leq T/D \leq 2$ and a structure in which pores adjacent to one another communicate with one another therein; and the supporting porous membrane has continuous pores with an average pore diameter of 0.5 D (μm) or more.

(2) The composite membrane according (1) above, wherein the porous membrane has an average membrane thickness T (μm) of $0.1 \leq T \leq 50$, and the supporting porous membrane has an average pore diameter of 1 μm or more.

(3) The composite membrane according to (1) or (2) above, wherein the porous membrane has an average pore diameter D (μm) of $0.1 \leq D \leq 20$ and an average membrane thickness T (μm) of $0.1 \leq T \leq 20$, and the supporting porous membrane has an average pore diameter between 1 and 100 μm and wherein a standard deviation σt (μm) of the membrane thickness is defined by $0 \leq \sigma t/T \leq 0.5$.

(4) The composite porous membrane according to any one of (1) to (3) above, wherein the porous membrane has an opening ratio between 15% and 80% and an average pore diameter D (μm) of $0.5 \leq D \leq 20$.

(5) A blood filtration membrane comprising the composite porous membrane according to any one of (1) to (4) above.

(6) A cell culture diaphragm comprising the composite porous membrane according to any one of (1) to (4) above, which partitions different cell groups in a cell culture solution so that the different cell groups come into contact with each other, and which is used for co-culture of the cells.

(7) A process for producing the composite porous membrane according to any one of claims (1) to (4), which comprises steps of: allowing a supporting porous membrane to retain a liquid that is not compatible with a solution of an organic polymer in a hydrophobic organic solvent; casting the solution of the organic polymer in the hydrophobic organic solvent on the supporting porous membrane; and evaporating the hydrophobic organic solvent in an environment wherein a relative humidity is between 20% and 100% near the membrane, so as to form a porous membrane containing the above described organic polymer as a main component on the supporting porous membrane.

(8) The process according to (7) above, wherein the liquid that is not compatible with the solution of the organic polymer in the hydrophobic organic solvent is water.

(9) A process for producing a hemocyte suspension from which leukocytes have been removed, which comprises: passing a hemocyte suspension to be treated through a first filter with a capability of removing leukocytes between 1.0 and 3.5 for 450 cm³ of the hemocyte suspension to be treated;

and then passing the whole hemocyte suspension discharged from the first filter through a second filter comprising one or more composite porous membranes according to any one of (1) to (4) above.

(10) A leukocyte removal filter device comprising a first filter disposed on the entrance side of the hemocyte suspension to be treated and a second filter disposed on the exit side thereof, wherein the first filter has a capability of removing leukocytes between 1.0 and 3.5 for 450 cm$^3$ of the hemocyte suspension to be treated, and the second filter comprises one or more composite porous membranes according to any one of (1) to (4) above.

(11) The leukocyte removal filter device according to (10) above, wherein the effective area of the second filter is between 4 and 300 cm$^2$.

(12) The leukocyte removal filter device according to (10) or (11) above, which has a filter element with a volume between 2 and 18 cm$^3$.

(13) The leukocyte removal filter device according to any one of (10) to (12) above, which has a capability of removing leukocytes of 4.0 or more for 450 cm$^3$ of the hemocayte suspension to be treated.

(14) A process for culturing cells, which comprises: disposing the composite porous membrane according to any one of (1) to (4) above in a cell culture solution to establish at least two culture regions; introducing different cell groups into the at least two culture regions adjacent to each other, respectively, and co-culturing the cells.

Effects of the Invention

The composite porous membrane of the present invention comprises a porous membrane and a supporting porous membrane. Such a porous membrane that controls size separation has a pore size of micron order, high pore size uniformity, and high opening ratio. The thickness of such a porous membrane is thin, and it has high uniformity. The inside of the porous membrane has a structure causing low filtration resistance. In addition, since a supporting porous membrane imparts sufficient mechanical strength, the composite porous membrane of the present invention brings on easy handlability in use, and thus it can be processed into various types of membrane forms. As a result, the use of the composite porous membrane of the present invention enables effective and efficient precise size filtration of various types of cells. Moreover, a leukocyte removal filter device using the present composite porous membrane enables significant reduction in the volume of a filter element while maintaining high capability of removing leukocytes. Thus, this device enables drastic reduction in the loss of a hemocyte suspension (whole blood, an erythrocyte product, a thrombocyte product, a blood plasma product, etc.) caused by the volume of filter element during filtration, and cost performance regarding blood products is thereby drastically improved in medical sites.

Furthermore, the use of the composite porous membrane of the present invention as a cell culture diaphragm enables effective intracellular contact with different cells via a thin uniform porous membrane, while maintaining a state where different cell groups are not mixed with one another and are kept separated in a cell culture solution. Accordingly, effective growth of cells of interest (for example, the growth in number of cells in a state where differentiation thereof is suppressed) can be achieved by contact with different cells. Further, since the supporting porous membrane imparts sufficient mechanical strength, the use of such a composite porous membrane with a large area suitable for practical cell growth, or processing thereof into various types of membrane forms, can be easily achieved. As a result, this composite porous membrane enables the growth of cells of interest in high volume and easy separation operation after the growth thereof.

BEST MODE FOR CARRYING OUT THE INVENTION

Figure 1:
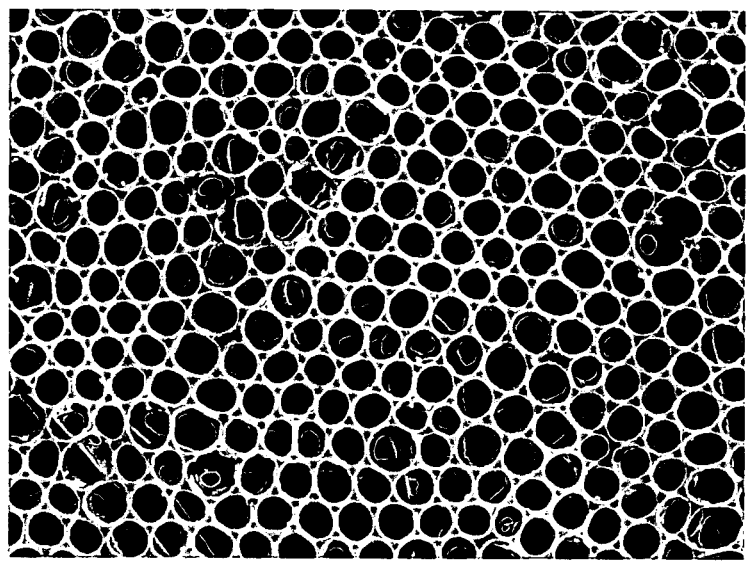
FIG. 1 is a scanning electron photomicrograph (1,000-fold) showing the surface on the porous membrane side of a composite porous membrane obtained in Example 1.

The present invention will be described in detail below.

The composite porous membrane of the present invention comprises at least one porous membrane containing an organic polymer and at least one supporting porous membrane adjacent thereto.

The composite porous membrane may have a structure wherein a porous membrane is adjacent to and also adheres to a supporting porous membrane (a structure wherein a porous membrane penetrates into a supporting porous membrane). Examples of such a structure may include: a bilaminar structure formed by integrating a single porous membrane with a single supporting porous membrane (that is, a structure consisting of "porous membrane/supporting porous membrane"); a trilaminar sandwich structure wherein porous membranes are located on both sides of a supporting porous membrane (that is, a structure consisting of "porous membrane/supporting porous membrane/porous membrane"); a trilaminar sandwich structure wherein supporting porous membranes are located on both sides of a porous membrane (that is, a structure consisting of "supporting porous membrane/porous membrane/supporting porous membrane"); and a trilaminar structure wherein two porous membrane layers are present on either one side of a supporting porous membrane (that is, a structure consisting of "porous membrane/porous membrane/supporting porous membrane"). A bilaminar structure formed by integrating a single porous membrane with a single supporting porous membrane (that is, a structure consisting of "porous membrane/supporting porous membrane") is preferable because it is easily produced.

First, the porous membrane containing an organic polymer (which is not a supporting membrane) of a composite porous membrane will be described.

When a pore of the porous membrane is observed from a direction vertical to the porous membrane flat surface, the pore has a round shape, unless external force is given (for example, pulling the composite porous membrane itself in a uniaxial direction). Depending on the composition of a hydrophobic organic solvent solution or production conditions (for example, the level of gas blowing), the shape of the pore may be somewhat deformed and may have an elliptical shape. The round shape defined in the present invention includes such an elliptical shape as well as a completely round shape.

When the porous membrane flat surface is observed with a photomicrograph, the porous membrane has an opening ratio between 10% and 90%, an average pore diameter D (μm) of $0.1 \leq D \leq 50$, and a standard deviation of pore diameter σd (μm) of $0 \leq \sigma d/D \leq 0.6$. The percentage of through-pores to all pores of the porous membrane is 30% or more. When the membrane section thereof is observed with a photomicrograph, the porous membrane has an average membrane thickness T (μm) of $0.05 \leq T/D \leq 2$. The porous membrane adopts a structure whereby pores communicate with pores adjacent thereto in the porous membrane. Membranes, whose opening ratio, D, σd, the percentage of through-pores, T, and internal membrane structure can not be experimentally determined, are excluded from the porous membrane of the present invention. For example, in the case of a non-woven fabric that is preferably used as a supporting porous membrane or a porous body having continuous pores in a three-dimensional network state that is mainly obtained by the phase separation method, it is difficult to determine the aforementioned factors by the methods described in examples. Accordingly, these products clearly differ from the porous membrane of the present invention.

The plane of the porous membrane has an opening ratio between 10% and 90%, preferably between 15% and 80%, more preferably between 20% and 70%, and most preferably between 25% and 60%. If such an opening ratio is less than 10%, a filtration rate may become slow, or contact efficiency between different cells separated from each other may decrease. In contrast, if such an opening ratio exceeds 90%, the strength of the porous membrane is significantly reduced, thereby causing membrane break or the like.

The value of an average pore diameter D (μm) is $0.1 \leq D \leq 50$, preferably $0.1 \leq D \leq 20$, more preferably $0.5 \leq D \leq 20$, and most preferably $0.8 \leq D \leq 10$. If the value of D exceeds 50 μm, it becomes difficult to separate ordinary cells of micron size or the like, and further, it may be difficult to effectively separate different cells from each other. In contrast, if the value of D is smaller than 0.1 μm, pores are too small to efficiently separate cells in a short filtration time, and further there are some cases where the contact efficiency between different cells separated from each other may decrease.

The standard deviation of pore diameter σd (μm) is $0 \leq \sigma d/D \leq 0.6$, preferably $0 \leq \sigma d/D \leq 0.5$, more preferably $0 \leq \sigma d/D \leq 0.4$, and most preferably $0 \leq \sigma d/D \leq 0.3$. If the value of σd/D exceeds 0.6, the size of a pore diameter becomes widely distributed, and it becomes insufficient to efficiently separate target substances to be separated. In addition, it results in insufficient precise size separation performance.

The composite porous membrane of the present invention is characterized in that an organic polymer constituting the porous membrane penetrates into a supporting porous membrane at least in a part of the supporting porous membrane flat surface adjacent to the porous membrane. For example, when the supporting porous membrane constituting the composite porous membrane is a non-woven fabric, if the surface of the porous membrane in the composite porous membrane is observed under an electron microscope, a state (clogging pore structure) where the shape of a pore is distorted or such a pore is occluded on the back side of the porous membrane (supporting porous membrane side) can be seen as a result of the porous membrane penetrating into a part of the non-woven fabric plane (a fibrous portion or an entangled fiber portion).

Figure 2:
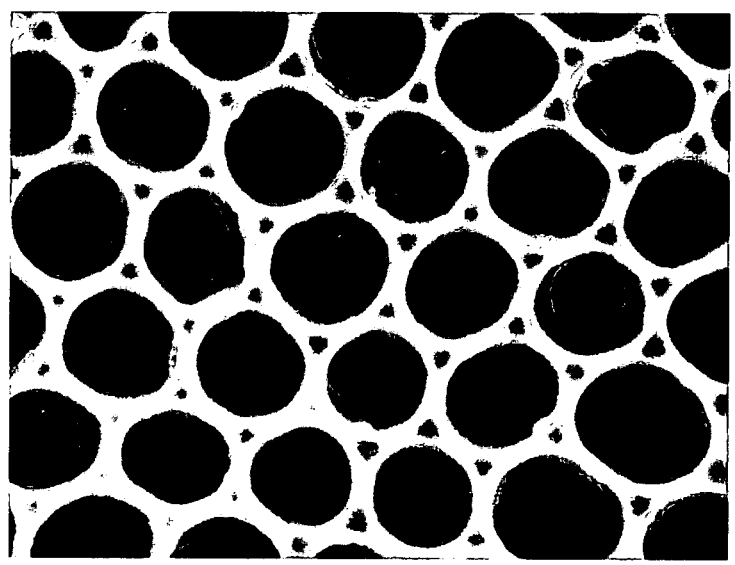
FIG. 2 is a scanning electron photomicrograph (3,000-fold) showing the surface on the porous membrane side of a composite porous membrane obtained in Example 1.

That is to say, in the composite porous membrane of the present invention, since the organic polymer constituting the porous membrane penetrates into a part of the supporting porous membrane, such a part of the supporting porous membrane (which is, for example, fibers constituting a non-woven fabric) decreases the through-pore percentage of the porous membrane and occludes pores (such a state is shown in FIGS. 1 and 2). As a result, it is extremely rare that all the pores of the porous membrane are through-pores.

In the composite porous membrane of the present invention, the percentage of through-pores in the porous membrane is 30% or more, preferably 40% or more, more preferably 50% or more, and most preferably 60% or more. If the ratio of such through-pores is less than 30%, not only a filtration rate or the contact efficiency between different cells separated from each other decreases, but also targets generally passing through such through-pores remain incorporated into clogging pores and captured therein. Thereby, the size separation effect decreases. It is to be noted that the percentage of through-pores in the porous membrane is also affected by membrane formation conditions (for example, the concentration of a hydrophobic organic solvent solution to be casted, the amount casted, the type of a solvent, etc.).

In the present invention, the term "through-pores" of the porous membrane is used to mean that when any given pore P is focused in the porous membrane, if the area of the pore P that is actually measured in the electron photomicrograph of the porous membrane flat surface (for example, when the shape of a pore is round, the value of $(D/2)^2\pi$ calculated from the diameter D of the pore) is defined as S(P), the area of a region (so-called through region) wherein the structure of the supporting porous membrane located on the other side can be observed through the pore P makes up 70% or more of S(P).

In the present invention, the term "percentage of through-pores" is used to mean the percentage of through-pores to all pores that can be observed in the electron photomicrograph of the porous membrane flat surface. For example, the expression "the penetrating rate of pores is 50%" is used to mean that when there are 10 pores, 5 pores of them are "through-pores."

The average membrane thickness T (μm) of the porous membrane can be measured by observing the section of the composite porous membrane under a microscope (mainly, an electron microscope). The value is $0.05 \leq T/D \leq 2$. It is preferably $0.1 \leq T \leq 50$, more preferably $0.1 \leq T \leq 20$, further more preferably $0.5 \leq T \leq 20$, and most preferably $0.8 \leq T \leq 10$. If the value of T is less than 0.1, the strength of the porous membrane decreases, and it is likely to become a cause of membrane break during filtration. In contrast, if the value of T exceeds 50, it becomes difficult for different cells separated from each other to come into contact with each other. In addition, since the membrane thickness correlates with average pore diameter D, the pore size necessarily increases, and thus it becomes difficult to separate ordinary cells of micron size or the like.

The standard deviation σt (μm) of membrane thickness is $0 \leq \sigma t/T \leq 0.5$, preferably $0 \leq \sigma t/T \leq 0.4$, and more preferably $0 \leq \sigma t/T \leq 0.3$. If the value of σt/T exceeds 0.5, it results in a wide distribution of membrane thickness, and contact between different cells separated from each other becomes partially difficult. Thus, effective contact becomes difficult in some cases.

Figure 4:
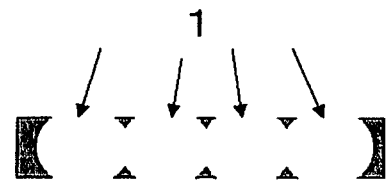
FIG. 4 is a conceptual diagram showing the section of a porous membrane having swelled spherical through-pores therein.

The pores of the porous membrane are characterized in that they communicate with pores adjacent thereto in the membrane. For example, the structure of a porous membrane section is preferably an internal spherical structure as shown in FIG. 4 (an inwardly swollen structure). As a result, since pores communicate with pores adjacent thereto (spherical through-pore 1), when compared with an independent cylindrical structure such as an etched membrane, the filtration resistance of a fluid significantly decreases in the porous membrane, thereby obtaining high filtration efficiency. In addition, even in a case where a part of the supporting porous membrane inhibits through-pore percentage when the above membrane is integrated with the supporting porous membrane, since pores communicate with one another in the direction of the membrane flat surface, even pores whose formation of through-pore is inhibited by the supporting porous membrane are able to contribute to filtration. It is not necessary that all the pores of the porous membrane be communicated with pores adjacent thereto in the membrane. However, as such a communicated space increases, the filtration resistance of a fluid favorably decreases. Such a communicated structure can be seen by observing the section of a composite porous membrane under a microscope (mainly, an electron microscope), as in the case of membrane thickness.

A process for producing such a membrane structure is not particularly limited. However, since a portion in which pores communicate with pores adjacent thereto can be often seen in a porous membrane produced by a membrane formation method using a water droplet as a template, as described later, such a membrane formation technique can be preferably used for production of the composite porous membrane of the present invention.

The type of an organic polymer forming the porous membrane is not limited, as long as it is dissolved in a hydrophobic organic solvent used. Examples of such an organic polymer may include: single materials including polyesters such as polylactic acid, polyhydroxyacetic acid, polycaprolactone or polyethylene adipate, polyurethanes, poly(meth)acrylic esters, polyvinyl acetals, polyamides, polystyrenes, polysulfones, cellulose derivatives, polyphenylene ethers, and polycarbonates; a polymer alloy or a blend consisting of two or more types selected from among the above substances; and a copolymer consisting of monomers forming the aforementioned polymer. However, the examples are not limited thereto.

Next, a supporting porous membrane will be described.

When a composite porous membrane is used as a filtration membrane, such a supporting porous membrane has functions to support and reinforce the porous membrane and to impart sufficient mechanical strength to the composite porous membrane, without impairing the filtration rate. Accordingly, it is preferable that an average pore size be large. In addition, when a composite porous membrane is used as a cell culture diaphragm, the supporting porous membrane has mechanical strength and, in some cases, also has the function as a scaffolding for cultured cells. In addition, in order to enable intracellular contact via the porous membrane, it is preferable that the supporting porous membrane has a pore size sufficient for cells to move therein. Accordingly, the supporting porous membrane has continuous pores with an average pore size of 0.5 D (µm) or more, preferably 1 µm or more, and more preferably between 1 and 100 µm. If such an average pore size is less than 0.5 D (µm), there are cases where an efficient filtration rate is hardly obtained or where it becomes difficult for cells to move and thus effective intracellular contact through the porous membrane becomes difficult. In contrast, such an average pore size exceeds 100 µm, there are cases where the supportability of the supporting porous membrane decreases because of decrease in adhesiveness of the porous membrane to the supporting porous membrane.

Such an "average pore size" is a value measured in accordance with the bubble point method described in ASTM-F316-86, using a Palm Porometer (manufactured by Porous Materials, Inc.).

The term "continuous pores" is used to mean pores communicated from one membrane flat surface of a supporting porous membrane to the other membrane flat surface on the opposite side. The shape of a pore on the membrane surface or the internal membrane structure thereof is not particularly limited, as long as a liquid or gas passes through such continuous pores.

If the thickness of the supporting porous membrane constituting the composite porous membrane is too large, processability into various filter forms decreases. In addition, there are some cases where the filtration rate significantly decreases or where the mobility of cells decreases. Thus, the membrane thickness is preferably 5 mm or less, more preferably 3 mm or less, and most preferably 1 mm or less. If the supporting porous membrane is too thin, it cannot play a role as a supporting layer in some cases. Accordingly, the thickness of the supporting porous membrane is preferably 1 µm or more, more preferably 5 µm or more, and most preferably 10 µm or more.

Specific examples of such a supporting porous membrane may include: non-woven fabrics obtained from natural fibers, synthetic polymer fibers, regenerative polymer fibers, inorganic fibers including a glass fiber as a typical example, organic/inorganic composite fibers, or the like; and porous bodies (porous membranes) having three-dimensional network continuous pores, which are obtained from organic polymer materials that are fused by heating, dissolved in a solvent in the form of a solution, or plasticized using a plasticizer, according to the foaming method, the phase separation method (thermotropic phase separation method or wet phase separation method), the drawing method, the sintering method, or the like. Further examples may include: woven fabrics or kitted fabrics obtained from natural fibers, synthetic polymer fibers, regenerative polymer fibers, glass fibers, organic/inorganic composite fibers, etc.; and various types of meshes consisting of an organic material, an inorganic material, a metal material, or a hybrid material thereof.

Examples of an organic polymer material used for the supporting porous membrane may include polyalkylene terephthalates, polycarbonates, polyurethanes, poly(meth)acrylic esters, polyacrylonitrile, polyvinyl alcohol, polyvinyl acetal, polyesters, polyamides, polystyrene, polysulfones, cellulose and cellulose derivatives, polyphenylene ethers, polyethylene, polypropylene, polyvinyl fluoride, polyvinyl chloride, polyvinylidene fluoride, and a copolymer consisting of monomers constituting these substances, and an alloy and a blend consisting of one or more types of the aforementioned polymers. However, the material of the supporting porous membrane of the present invention is not limited to the aforementioned examples.

Preferred examples of such a supporting porous membrane may include non-woven fabrics, woven fabrics, and meshes. Examples of an organic polymer material forming fibers constituting the supporting porous membrane may include polyethylene terephthalate, polypropylene, a cellulose derivative, polyamide, and polyacrylonitrile. Of these, polyethylene terephthalate is particularly preferable.

When the supporting porous membrane is not especially actively allowed to exhibit separation performance, in order to increase the filtration efficiency of a target solution to be filtrated, the supporting porous membrane preferably comprises crude continuous pores with low filtration resistance and has appropriate strength. Specific examples of such a supporting porous membrane may include a non-woven fabric, woven-fabric, mesh filters, obtained from organic polymer fibers. Of these, a non-woven fabric is preferable.

When such a non-woven fabric is used as a supporting porous membrane, if the fiber diameter thereof is too large, there are cases where the through-pore percentage of the porous membrane is inhibited, or where increased unevenness of a plane adhering to the porous membrane inhibits the smoothness or thickness uniformity of the porous membrane. In contrast, if the fiber diameter is too small, a portion adhering to the porous membrane decreases. Thereby, in some cases, the supporting porous membrane cannot sufficiently support or reinforce the porous membrane, or it cannot achieve strength sufficient as a composite porous membrane due to a decrease in the strength of the supporting porous membrane itself. Accordingly, the fiber diameter of a non-woven fabric is preferably between 0.1 and 50 µm, more preferably between 0.1 and 30 µm, further more preferably between 0.5 and 15 µm, and most preferably between 0.5 and 5 µm.

Moreover, if a non-woven fabric has too large a mass per unit area, there may be cases where it may inhibit the formation of through-pore of the porous membrane, where the filtration rate decreases, or where it becomes difficult for cells to move. On the other hand, if its mass per unit area is too small, there may be cases where the support or reinforcement of the porous membrane becomes insufficient, or where it cannot achieve strength sufficient as a composite porous membrane. Accordingly, when a non-woven fabric has a thickness of 200 µm for example, the mass per unit area thereof is preferably between 10 and 200 g/m$^2$, more preferably between 15 and 150 g/m$^2$, and further more preferably between 20 and 100 g/m$^2$.

When the supporting porous membrane is actively allowed to exhibit separation performance, for example, when the supporting porous membrane is applied to a filtration system wherein a solution to be filtrated is first passed through the supporting porous membrane and it is then separated by the porous membrane, the supporting porous membrane is allowed to exhibit the effect as a pre-filter of separating or adsorbing particles greater than those separated by the porous membrane, thereby preventing the porous membrane from being clogged or increasing the separation efficiency.

The composite porous membrane of the present invention is formed by integrating a porous membrane with a supporting porous membrane. An organic polymer constituting the porous membrane penetrates into at least a portion of the surface of the supporting porous membrane adjacent to the porous membrane, so that a structure wherein the two membranes adhere to each other can be formed. The presence of such a structure can be confirmed by observing the porous membrane under an electron microscope. The presence of such a structure enables high adhesiveness between the porous membrane and the supporting porous membrane.

Furthermore, the composite porous membrane may also have a structure wherein both lateral faces of the supporting porous membrane are sandwiched with the porous membranes. In such a case, the average pore diameter, opening ratio, or substances constituting both porous membranes may be identical to or different from each other.

If the thickness of the composite porous membrane of the present invention is too thick, processing properties for processing into various types of forms decreases, and the filtration rate may further decrease. Thus, the membrane thickness is preferably 5 mm or less, more preferably 3 mm or less, and most preferably 1 mm or less. On the other hand, if such a thickness is too thin, handlability or processability decreases. Thus, the membrane thickness is preferably 1 µm or more, more preferably 5 µm or more, and most preferably 10 µm or more.

Since the composite porous membrane of the present invention has strength sufficient for processing, the plane membrane form may also be processed into various types of forms such as a hollow, a bag, or a pleated form. For example, two slices of composite porous membranes with a square form of the same size are laminated such that a supporting porous membrane (for example, a non-woven fabric) is disposed inward, and the 3 sides thereof are then sealed by heat sealing, thereby obtaining a bag-form sheet, wherein the non-woven fabric exists therein and the entire periphery is covered with the porous membrane. Furthermore, a single composite porous membrane cut into the form of a sector is rounded, and two chords are then sealed by heat sealing, so as to obtain a funnel structure (conical structure). A rectangular composite porous membrane is rounded, and the attached two sides are then sealed by heat sealing, so as to obtain a tubular form (hollow form). This product can be used for various purposes.

Further, the composite porous membrane can also be processed into a state where it is integrated with another member. For example, the composite porous membrane is allowed to adhere to the end face of a tube made from a glass or plastic by adhesion or fusion adhesion using an adhesive agent, so as to integrate the composite porous membrane with the tube. If the composite porous membrane is allowed to adhere to the end face of a tube, it can be processed into a cup-type container. Otherwise, the composite porous membrane is allowed to adhere to both ends, so as to produce a sealed container.

The composite porous membrane may be used singly (one slice). Several composite porous membranes may be laminated, so as to construct various types of laminar structures and used them. Still further, by overlaying one or more composite porous membranes on one or more supporting porous membranes constituting them (by combining one or more composite porous membranes with one or more supporting porous membranes constituting them), it becomes possible to provide membrane materials with various performances.

Next, a process for producing the composite porous membrane of the invention of the present application will be described.

Processes for integrating a porous membrane with a supporting porous membrane include: (1) a process comprising preparing a porous membrane and a supporting porous membrane separately and then allowing the porous membrane to adhere to the supporting porous membrane; and (2) a process comprising forming a porous membrane on a supporting porous membrane and then simultaneously conducting adhesion and formation of a membrane. The method described in (2) above enables production of a composite porous membrane that has been simply integrated without decreasing strength or permeation rate.

The process for producing the composite porous membrane of the present invention comprises 3 processes of: (a) allowing a supporting porous membrane to retain a liquid that is not compatible with a solution of an organic polymer in a hydrophobic organic solvent; (b) casting the solution of the organic polymer in the hydrophobic organic solvent on the supporting porous membrane; and (c) evaporating the hydrophobic organic solvent in an environment wherein a relative humidity is between 20% and 100% near the liquid face, so as to form a porous membrane containing the above described organic polymer as a main component on the supporting porous membrane.

The expression "solution of an organic polymer in a hydrophobic organic solvent" is used in the present invention to mean a solution obtained by dissolving in a hydrophobic organic solvent, an organic polymer used as a main component of a porous membrane formed on a supporting porous membrane. The concentration of such a solution is preferably between 0.01 and 30 wt %, more preferably between 0.03 and 15 wt %, and most preferably between 0.04 and 5 wt %. If the concentration is less than 0.01 wt %, there are cases where the pore regularity of the porous membrane decreases or where membrane strength decreases. On the other hand, if the concentration exceeds 30 wt %, there are cases where a regular honeycomb structure is hardly formed. In addition, in order to form through-pores, the amount of the "solution of an organic polymer in a hydrophobic organic solvent" casted on the supporting porous membrane must be significantly reduced, so as to decrease the membrane thickness. This causes extremely high difficulty in membrane formation techniques, and thus it is not favorable.

The type of such a "hydrophobic organic solvent" is not limited, as long as it is an organic solvent that is not compatible (homogenized) with water at any given ratio, in which an organic polymer forming a porous membrane is dissolved. However, since such a solvent is evaporated at a relative humidity between 20% and 100%, a hydrophobic solvent with high volatility, which makes evaporation and elimination relatively easy, is preferably used. Examples of such a solvent may include: halogen organic solvents including chlorides or fluorides such as chloroform, dichloromethane, or dichloroethane; hydrocarbon solvents such as benzene, toluene, xylene, n-hexane, cyclohexane, methylcyclohexane, or decalin; ester solvents such as ethyl acetate or butyl acetate; and water-insoluble ketone solvents such as methyl isobutyl ketone. These solvents are used singly or in the form of a mixture consisting of two or more types. Of these, chloroform, dichloromethane, and toluene are preferable. In particular, chloroform and dichloromethane are more preferable because many types of organic polymers can be dissolved therein and evaporation and elimination is easily conducted. However, when chloroform or dichloromethane is used, since the specific gravity thereof is considerably greater than that (specific gravity 1) of a micro water droplet used as a template for pores, there are cases where the porous membrane hardly has through-pore form. In such a case, a different solvent capable of adjusting the specific gravity of a solution, such as toluene, may previously be added to chloroform at an amount between 1% and 20% by weight. Such an addition is effective for formation of through-pores.

According to the present invention, first, (a) a supporting porous membrane is allowed to retain a liquid that is not compatible with a solution of an organic polymer in a hydrophobic organic solvent. When such a hydrophobic organic solvent solution is casted on the supporting porous membrane, it is necessary that the hydrophobic organic solvent solution does not penetrate into the pores of the supporting porous membrane and occlude them. As a method of achieving this, a liquid that is not compatible with the hydrophobic organic solvent solution has previously been retained by the supporting porous membrane, and the internal pores of the supporting porous membrane are thereby filled with the above liquid. In particular, in the case of using a supporting porous membrane having crude continuous pores, which is preferable as the supporting porous membrane of the present invention (for example, a non-woven fabric or woven-fabric), the above method is effective for prevention of easy permeation of a hydrophobic organic solvent solution casted on the supporting porous membrane. Since penetration of the hydrophobic organic solvent solution into the supporting porous membrane is prevented, the solution can be thinly and smoothly casted on the supporting porous membrane. As a result, the porous membrane can be thinly, uniformly, and smoothly formed on the supporting porous membrane, and ultimately, an organic polymer does not occlude the supporting porous membrane.

The term "liquid that is not compatible with a hydrophobic organic solvent solution" (hereinafter referred to as "incompatible liquid" at times) is used to mean a liquid, which does not become a homogeneous solution when it is mixed with the above solution at a certain amount, and in which almost no organic polymer as a main component of the porous membrane is dissolved. Such an incompatible liquid is not limited but is selected depending on the type of a hydrophobic organic solvent used. An incompatible liquid that can be easily eliminated from the inside of the supporting porous membrane by drying or washing after formation of the porous membrane is preferable.

When the affinity for a water droplet as a template is high, the porous membrane easily forms through-pores. Thus, preferred examples of the aforementioned incompatible liquid may include water, an aqueous solution containing various types of salts such as sodium chloride, a water-soluble liquid polymer such as polyethylene glycol, and an aqueous solution containing them.

In order to treat such an incompatible liquid in the industrial field, those having a simple composition are preferable. Among others, water is particularly preferable. It is required for such an incompatible liquid not to dissolve an organic polymer. However, when a hydrophobic organic solvent solution is allowed to come into contact with the above liquid during formation of the membrane, if an organic polymer contained in the hydrophobic organic solvent solution does not substantially move to the above liquid, the above liquid may dissolve a small extent of such an organic polymer.

As a method for allowing the supporting porous membrane to retain a liquid that is not incompatible with the hydrophobic organic solvent solution, the supporting porous membrane has been sufficiently immersed in this liquid in advance, and it is then removed from the liquid and used. (If ultrasonic wave is applied during such immersion, the above liquid can be more effectively retained in the supporting porous membrane.) Otherwise, before the casting of the hydrophobic organic solvent solution, the above liquid may be directly dropped onto the supporting porous membrane, or may be sufficiently sprayed to the supporting porous membrane.

Thereafter, (b) the solution of the organic polymer in the hydrophobic organic solvent is casted on the supporting porous membrane. As a casting method, any method can be applied, as long as it comprises uniformly and completely casting the above solution on the supporting porous membrane. Thus, such a method is not particularly limited. When the viscosity of the solution is low, it is directly casted on the supporting porous membrane. When the viscosity is high, it is uniformly casted using a blade coater or the like.

For the purpose of improving the membrane formation stability or strength of the porous membrane, modifying the surface thereof (for example, imparting hydrophilicity thereto), or imparting toughness thereto, other additives may be added, as long as they are substances that can be dissolved in the hydrophobic organic solvent solution used in the present invention. For example, when one or more types of amphipathic compounds, such as bis(hexadecyl)ammonium bromide described in Mater. Sci. Eng., Vol. C8-9, p. 495 (1999), are added, the membrane formation stability, pore size, and pore shape uniformity of the porous membrane preferably increase. In particular, a polyacrylamide amphipathic compound represented by the following structural formula (I) is a preferable example.

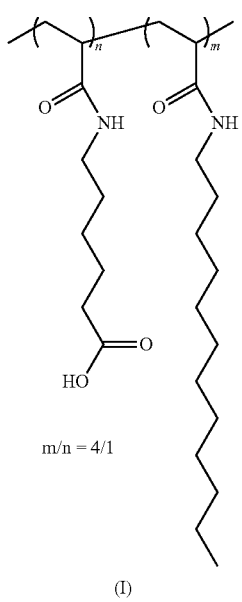

[Formula 1]

m/n = 4/1

(I)

When the aforementioned amphipathic compound is added to the hydrophobic organic solvent solution, the composition ratio between the organic polymer and the amphipathic compound (organic polymer/amphipathic compound (wt/wt)) is not limited. It is preferably between 99/1 and 50/50 (wt/wt). If the ratio of the amphipathic compound is smaller than 99/1, a uniform porous membrane is hardly formed. If the above ratio is greater than 50/50, the strength of the porous membrane decreases, thereby causing membrane break.

Subsequently, (c) a hydrophobic organic solvent is evaporated from the hydrophobic organic solvent solution casted on the supporting porous membrane in an environment wherein the relative humidity around the liquid face is between 20% and 100%, and during this process, a porous membrane having a honeycomb pore structure is formed.

As a method of evaporating such a hydrophobic organic solvent, any method may be applied, as long as the relative humidity around the liquid face (a position approximately 2 cm apart from the liquid face in the vertical direction during formation of a membrane) is adjusted between 20% and 100%. Examples of such a method may include a method of increasing the temperature in the peripheral environment of membrane formation, a method of appropriately decreasing the atmospheric pressure in the membrane formation environment, and a method of gently blowing suitable gas to the liquid face. Of these, the method of blowing gas to the liquid face is preferable because formation of a micro water droplet used as a template of the porous membrane is easy, and also because humidity is easily controlled and a simple device is thereby used.

When gas is blown to the liquid face to evaporate the organic solvent, any type of gas may be used, as long as it is blown to the hydrophobic organic solvent solution, so as to effectively evaporate the hydrophobic organic solvent. Gas that is chemically inactive to the porous membrane, the supporting porous membrane, and the hydrophobic organic solvent solution during the membrane formation process, is preferable. Specific examples of such gas may include air, nitrogen, oxygen, helium, argon or the like, and mixed gas thereof. Taking into consideration cost performance, air is preferable.

As a method of blowing gas to the hydrophobic organic solvent solution, a method of establishing a pump on the gas-supplying side, supplying gas through a suitable nozzle, and blowing it, is used. In the case of using a hermetically sealed thermo-hygrostat box or the like, a method of reducing the pressure in the box, aspirating gas from the outside, and then blowing the gas to the hydrophobic organic solvent solution through a suitable nozzle, is used.

When a hydrophobic organic solvent is evaporated by gas blowing or the like, such gas blowing is carried out in an environment wherein the relative humidity around the membrane is between 20% and 100%. Such relative humidity is preferably between 30% and 90%, and more preferably between 35% and 80%. When the relative humidity is less than 20%, the growth of a water droplet acting as a template for forming a pore is insufficient. Thus, a uniform honeycomb pore structure is hardly formed, and the through-pore percentage is also deteriorated.

Such "an environment wherein the relative humidity around the membrane is between 20% and 100%" may be set by adjusting the relative humidity of the membrane formation environment as a whole, such as in a thermo-hygrostat box. When a gas blowing method is applied, such an environment can be set by adjusting the relative humidity of the gas to be blown.

A hydrophobic organic solvent is evaporated, and during such a process, a micro water droplet forming on the surface of a solution acts as a template, so as to form a porous membrane having a uniform pore structure is formed on the supporting porous membrane. After formation of pores, the liquid retained by the supporting porous membrane is directly removed by drying, or it is once immersed in alcohol or the like for liquid substitution, and it is then removed by drying.

Various types of surface modification can be performed on the supporting porous membrane used in the production process of the present invention or the obtained composite porous membrane, depending on various requirements in production process or in use, such as the improvement of water permeability, the improvement of separability by introduction of a selective functional group, or suppression of the adhesiveness of biological substances or the like.

In particular, in the case of the production process of a composite porous membrane preferably used in the present invention, namely, a production process comprising allowing the supporting porous membrane to retain water to form a porous membrane, if the hydrophobicity of the supporting porous membrane is strong, it becomes impossible to allow the supporting porous membrane to uniformly retain water thereon. Thus, a hydrophobic organic solvent solution used for forming a porous membrane penetrates into the supporting porous membrane, and thereby, it becomes difficult for the supporting porous membrane to smoothly retain the above hydrophobic organic solvent solution thereon. Accordingly, there are some cases where it becomes difficult to produce a composite porous membrane with a desired form. In such a case, it is preferable that a hydrophilic treatment be performed on the surface of the supporting porous membrane, so as to enhance water retentivity.

For the aforementioned reasons in terms of production, when a hydrophilic treatment has previously been performed on the supporting porous membrane, or when such a hydrophilic treatment is performed for the improvement of the performance of the obtained composite porous membrane in practical use (the improvement of water permeability, blood compatibility, protein non-adsorptive properties, etc.), it is preferable to introduce a suitable hydrophilic functional group on the surface of the membrane, as necessary.

Moreover, for example, when a composite porous membrane is used as a blood filtration membrane or a filter element of a leukocyte removal filter, it is effective for the improvement of the performance to introduce in a well-balanced manner, both a hydrophilic functional group for suppressing non-selective adsorption of blood cell components and a nitrogen-containing basic functional group for expressing selective affinity for leukocytes.

The term "hydrophilic functional group" is used herein to mean a functional group having affinity for water molecules. Such a hydrophilic functional group includes various types of know hydrophilic functional groups. Specific examples may include functional groups having relatively high hydrophilicity, such as an alcoholic hydroxyl group, a phenol hydroxyl group, a carboxyl group, a sulfone group, a carbonyl group, an ester group, an ether group, an amide group, an N-monosubstituted amide group, and an N,N-disubstituted amide group. It is preferable to introduce these hydrophilic functional groups, singly or in combination of two or more types. It is particularly preferable to introduce nonionic hydrophilic functional groups such as an alcoholic hydroxyl group, a carbonyl group, an ester group, an ether group, an amide group, or an N—N-disubstituted amide group, singly or in combination of two or more types.

Examples of a "nitrogen-containing basic functional group" introduced for the purpose of expressing selective affinity for leukocytes may include nitrogen-containing aromatic groups such as an aliphatic primary amino group, an aliphatic secondary amino group, an aliphatic tertiary amino group, a pyridyl group, a bipyridyl group, or an imidazole group. It is preferable to introduce these nitrogen-containing basic functional groups, singly or in combination of two or more types. Since such an aliphatic primary amino group ($—NH_2$), an aliphatic secondary amino group, and an aliphatic tertiary amino group have lower hydrophobicity than that of an aromatic amino group, it is particularly preferable to use such aliphatic amino groups to realize selective affinity for leukocytes. Specifically, such an aliphatic secondary amino group has the structure $—NHR^1$, wherein $R^1$ is not particularly limited but may have any structure. Examples may include linear alkyl groups such as a methyl group, an ethyl group, or a propyl group, and branched alkyl groups such as an isopropyl group. The number of carbon atoms or structure of such an alkyl group is not particularly limited. In addition, one or more hydrogen atoms thereof may also be substituted with any given functional groups having a hydroxyl group, an ester group, a carbonyl group, or an ether group. Moreover, such an aliphatic tertiary group has the structure $—NR^2R^3$, wherein $R^2$ and $R^3$ may have various structures as with $R^1$, and further where $R^2$ and $R^3$ may be either identical to or different from each other.

Among them, an aliphatic tertiary amino group has a preferred structure, and thus a functional group having such an aliphatic tertiary amino group is effective as a leukocyte selective affinity functional group. Specific examples of such a functional group may include a dimethylamino group, a diethylamino group, an ethylmethylamino group, a diethanolamino group, a 2-(dimethylamino)ethyl group, a 3-(dimethylamino)propyl group, a 2-(diethylamino)ethyl group, and a 3-(diethylamino)propyl group.

Examples of a specific method of introducing a functional group such as a hydrophilic functional group or a nitrogen-containing basic functional group into the membrane surface may include: (a) a method of introducing a functional group of interest or the like into a functional group that is originally present on the surface of a membrane substrate by a polymer reaction; (b) a method of applying electron beam or γ-ray to the surface of a membrane substrate to generate radicals and then allowing a monomer having a functional group of interest to act on such radicals for graft polymerization; (c) various types of living polymerization methods, which comprise introducing a necessary initiator group into the surface of a membrane substrate and then adding a catalyst or the like as necessary (for example, the living radical polymerization method or the living anion polymerization method); and (d) a method of coating the surface of a membrane substrate by the immersion method or the spray method. In particular, the coating method described in (d) above is preferable because the type, amount, polymerization chain distribution of a functional group to be introduced can easily be designed during the synthetic reaction of a coating polymer, and also because such a coating process itself is simple, providing high productivity.

When a hydrophilic functional group is introduced into the supporting porous membrane or composite porous membrane by the coating method, the type of a hydrophilic functional group-containing monomer used for the synthesis of the coating polymer is not particularly limited. A monomer containing a nonionic hydrophilic functional group is particularly preferable. Examples of such a compound may include: (meth)acrylic esters having an alcoholic hydroxyl group, such as 2-hydroxyethyl methacrylate or 2-hydroxypropyl methacrylate; (meth)acrylamides including (meth)acrylamide, N-monosubstituted (meth)acrylamide, and N,N-disubstituted (meth)acrylamide such as N,N-dimethylacrylamide or N,N-diethylacrylamide; and (meth)acrylic esters of alkoxy polyethylene glycol having a polyoxyethylene group having 1 to 100 repeating units of $—CH_2CH_2O—$.

When the hydrophilicity of a coating polymer is too high, elution of a coating polymer into a filtrate or a cell culture solution in practical use causes a problem in many cases. (Such low elution properties are important particularly for the medical use.) It is preferable that for the purpose of suppression of such elution properties, other types of hydrophobic monomers are copolymerized at a suitable amount, so as to synthesize a coating polymer.

In addition, when a nitrogen-containing basic functional group is introduced into the supporting porous membrane or composite porous membrane by the coating method, the type of a monomer containing a nitrogen-containing basic functional group used for the synthesis of the coating polymer is not particularly limited. A monomer containing an aliphatic tertiary amino group is particularly preferable. Examples of such a compound may include 2-(dimethylamino)ethyl (meth)acrylate, 2-(diethylamino)ethyl(meth)acrylate, 2-(ethylmethylamino)ethyl(meth)acrylate, 2-(diethanolamino)ethylethyl(meth)acrylate, 2-(dimethylamino)propylethyl(meth)acrylate, 3-(dimethylamino)propyl(meth)acrylate, 3-(diethylamino)propyl(meth)acrylate, 2-(diethanolamino)propyl(meth)acrylate, and 3-(diethanolamino)propyl(meth)acrylate.

When the coating method is used as a method of modifying the surface of a supporting porous membrane used in the production process of the present invention or the surface of the obtained composite porous membrane, a coating polymer has previously been synthesized, and the coating polymer is then dissolved in a suitable solvent to prepare a coating solution.

Examples of a method of coating such a supporting porous membrane or composite porous membrane with a coating solution may include: a method of immersing a supporting porous membrane or composite porous membrane to be coated (a target membrane to be coated) in a coating solution; a method of setting a target membrane to be coated to a filter holder and then allowing a coating solution to pass through it; and a method of spraying such a coating solution to a target membrane to be coated. Of these, in order to easily conduct coating with high uniformity, the immersion method is preferable.

The type or composition of a coating polymer is not limited, as long as it is dissolved in a suitable solvent and then a necessary amount of hydrophilic functional group or nitrogen-containing basic functional group can be introduced by coating into at least the surface portion of a supporting porous membrane or composite porous membrane. Examples of such a coating polymer may include: a blend of a polymer obtained by polymerization of one or more types of the aforementioned hydrophilic functional group-containing monomers with a polymer obtained by polymerization of one or more types of nitrogen-containing basic functional group-containing monomers; and a copolymer obtained by copolymerization of one or more types of hydrophilic functional group-containing monomers with one or more types of nitrogen-containing basic functional group-containing monomers. When the coating polymer is a copolymer, it may be either a random copolymer or a block copolymer.

With regard to the molecular weight of such a coating polymer, the weight average molecular weight (Mw) is preferably between $1.0 \times 10^3$ and $2.0 \times 10^6$, more preferably between $5.0 \times 10^3$ and $1.5 \times 10^6$, and most preferably between $1.0 \times 10^4$ and $1.0 \times 10^6$. When Mw is less than $1.0 \times 10^3$, the entangling effect of molecular chains decreases, and immobilization on the surface portion of a porous membrane thereby becomes insufficient. Thus, there are some cases where a coating polymer is eluted when used. In contrast, when Mw exceeds $2.0 \times 10^6$, its solubility in a solvent decreases, and the uniformity of a solution may thereby decrease. In addition, the viscosity of a solution becomes too high, and there are some cases where it becomes impossible for the surface of a membrane material to be uniformly coated with the solution. Herein, Mw is a value obtained by the gel permeation chromatography method (GPC; relative to standard polystyrene).

The type of a solvent, in which a coating polymer is dissolved, is not limited, as long as the solvent does not cause significant swelling or dissolution of a supporting porous membrane or composite porous membrane, and in particular, a porous membrane constituting a composite porous membrane, and as long as the coating polymer is sufficiently dissolved therein, and ultimately the solvent is removed from the composite porous membrane or the supporting porous membrane. Thus, various types of solvents can be used depending on the type of a coating polymer. Examples of such a solvent may include: alcohols such as methanol, ethanol, propanol, or butanol; ketones such as acetone or methyl ethyl ketone; esters such as ethyl acetate; aromatic hydrocarbons such as benzene, toluene, or xylene; aliphatic hydrocarbons such as hexane, cyclohexane, methylcyclohexane, or decalin; halogenated hydrocarbons such as chloroform, dichloromethane, or dichloroethane; sulfur-containing solvents such as dimethyl sulfoxide; and amides such as N,N-dimethylformamide or N,N-dimethylacetamide. These solvents can be used singly or in combination of two or more types. Of these, alcohols are preferable in terms of moderate drying rate, handlability, and high affinity for a polymer having a hydrophilic functional group. In particular, ethanol is practically extremely preferable because it has low toxicity to human bodies. If necessary, an appropriate amount of water is mixed for the purpose of finely adjusting the hydrophilicity or hydrophobicity of a solvent.

When the coating method is used as a method of modifying the surface of a supporting porous membrane used in the production process of the present invention or the surface of the obtained composite porous membrane, a coating polymer has previously been synthesized, and the synthesized coating polymer is dissolved in a suitable solvent, so as to prepare a coating solution.

When a hydrophilic functional group or nitrogen-containing basic functional group has previously been introduced by coating into a supporting porous membrane, the concentration of a polymer in a coating solution is preferably between 0.01 wt % and 50 wt %, more preferably between 0.1 wt % and 30 wt %, and most preferably between 0.5 wt % and 20 wt %. If the concentration of a coating solution is less than 0.01 wt %, coating becomes insufficient, and the surface of the supporting porous membrane is thereby partially exposed. In contrast, if such a concentration exceeds 50 wt %, since the viscosity of a solution increases, it becomes difficult for the supporting porous membrane to be uniformly coated with the solution, or the pores of the supporting porous membrane are likely to be occluded.

When a hydrophilic functional group or nitrogen-containing basic functional group is introduced into the obtained composite porous membrane by coating, the concentration of a polymer in a coating solution is preferably between 0.01 wt % and 10 wt %, more preferably between 0.05 wt % and 5 wt %, and most preferably between 0.1 wt % and 1 wt %. If the concentration of a coating solution is less than 0.01 wt %, coating becomes insufficient, and the surface of the porous membrane is thereby partially exposed. In contrast, if such a concentration exceeds 10 wt %, since the viscosity of a solution increases, it becomes difficult for the porous membrane to be uniformly coated with the solution, or the pores of the porous membrane are likely to be occluded.

A preferred coating process comprises: immersing a supporting porous membrane or composite porous membrane for a certain period of time in a coating polymer solution that has previously been adjusted to a suitable concentration; removing it from the solution; and squeezing the membrane with a nip roll, or blowing air or nitrogen gas thereto, so as to remove an unnecessary coating polymer solution. Either a continuous process or a batch process can be adopted.

The time required for a supporting porous membrane or composite porous membrane to be immersed in a coating polymer solution is preferably between 0.5 and 60 seconds, more preferably between 1 and 30 seconds, and most preferably between 2 and 10 seconds. If such an immersion time is less than 0.5 seconds, there are cases where coating becomes ununiform and insufficient. Even if such an immersion time exceeds 60 seconds, the amount coated rarely increases. In addition, depending on the type of a porous membrane, there are cases where the porous membrane itself swells.

According to the production process of the present invention, since a porous membrane penetrates into fine unevenness on the surface of a supporting porous membrane (which is an entangled fiber portion in a case where the supporting porous membrane is a fiber medium such as a non-woven fabric or mesh) during the process of forming the porous membrane on the surface of the supporting porous membrane, it becomes possible to realize a state where the supporting porous membrane strongly adheres to a porous membrane. On the other hand, in a case where a porous membrane is once formed on a solid substrate such as a glass as with the conventional process, and where it is then peeled and overlaid on a supporting porous membrane, since the porous membrane does not adhere to the supporting porous membrane, a displacement is generated between both membranes by pulling them, for example, and as a result, the porous membrane is easily broken.

The composite porous membrane obtained by the production process of the present invention, which includes a porous membrane, has extremely high strength. Thus, it is extremely easy to handle the membrane, when it is used. In addition, the above composite porous membrane can be processed into various forms such as a roll-, cylindrical, or pleated-form, and then used.

Next, the leukocyte removal filter device of the present invention will be described.

The leukocyte removal filter device of the present invention is a filter device having a first filter located on the entrance side of a hemocyte suspension to be treated and a second filter located on the exit side thereof. The term "hemocyte suspension to be treated" is used to mean a hemocyte suspension before being filtrated with a filter.

The capability of the first filter to remove leukocytes is between 1.0 and 3.5, preferably between 1.3 and 3.3, and more preferably between 1.5 and 3.0, for 450 $cm^3$ of the hemocyte suspension to be treated.

In the case of the first filter, the "capability of removing leukocytes" is obtained using the following formula (1) based on the concentrations of leukocytes in a hemocyte suspension before and after filtration obtained when 450 $cm^3$ of the hemocyte suspension to be treated is passed through the first filter.

Capability of removing leukocytes=−log(a leukocyte concentration in the hemocyte suspension after filtration/a leukocyte concentration in the hemocyte suspension before filtration)  (1)

If the capability of the first filter of removing leukocytes is less than 1.0, the second filter consisting of a composite porous membrane may be occluded with large quantities of leukocytes. Moreover, if such occlusion of the second filter is intended to be prevented, the second filter with an extremely large area is required. Thus, the size of a leukocyte removal filter becomes significantly larger than the conventional level, and it becomes difficult to handle such a filter of large size in medical sites. In contrast, if the capability of the first filter of removing leukocytes exceeds 3.5, the volume of a filter element in the first filter becomes large, and thus, the "effect of reducing the loss of a hemocyte suspension by reduction in such a volume of filter element," which is the effect of the present invention, decreases.

When the amount of the hemocyte suspension to be treated used is too small, the ratio of the amount of a hemocyte suspension remaining in a filter after filtration to a certain amount of the hemocyte suspension to be treated (namely, the loss of a hemocyte suspension) increases, and thus it results in poor filtration efficiency. Accordingly, the amount of the hemocyte suspension to be treated used is preferably 15 $cm^3$ or more. If the amount of the hemocyte suspension to be treated used is too large, there are cases where the second filter consisting of a composite porous membrane is occluded with large quantities of leukocytes. If the amount is further larger, the presence of not only leukocytes but also large quantities of blood cell components causes significant reduction in the filtration rate of the first filter or occlusion thereof. Thus, the amount of the hemocyte suspension to be treated used is preferably 2,000 $cm^3$ or less. The amount of the hemocyte suspension to be treated is more preferably between 50 and 1,500 $cm^3$, further more preferably between 100 and 1,000 $cm^3$, and most preferably between 200 and 600 $cm^3$.

The first filter may have any structure, as long as the capability of removing leukocytes is between 1.0 and 3.5. As with the aforementioned specific examples of the supporting porous membrane of a composite porous membrane, specific examples of such a first filter may include: non-woven fabrics obtained from natural fibers, synthetic polymer fibers, regenerative polymer fibers, inorganic fibers including a glass fiber as a typical example, organic/inorganic composite fibers, or the like; and porous bodies (porous membranes) having three-dimensional network continuous pores, which are obtained from organic polymer materials that are fused by heating, dissolved in a solvent in the form of a solution, or plasticized using a plasticizer, according to the foaming method, the phase separation method (thermotropic phase separation method or wet phase separation method), the drawing method, the sintering method, or the like. Further examples may include: woven fabrics or kitted fabrics obtained from natural fibers, synthetic polymer fibers, regenerative polymer fibers, glass fibers, organic/inorganic composite fibers, etc.; and various types of meshes consisting of an organic material, an inorganic-material, a metal material, or a hybrid material thereof.

Of these, a non-woven fabric obtained from an organic polymer fiber, or a porous body obtained by the phase separation method, which forms relatively uniform three-dimensional continuous pores, is preferable.

Examples of the material of an organic polymer forming a non-woven fabric itself may include polyethylene terephthalate, polypropylene, a cellulose derivative, polyamide, and polyacrylonitrile. Of these, polyethylene terephthalate is particularly preferable.

In addition, as a fiber constituting such a non-woven fabric, an extra fine fiber is preferable. In terms of strength and ability to capture leukocytes, the fiber diameter is preferably between 0.3 and 3 μm, more preferably between 0.5 and 2 μm, and most preferably between 0.5 and 1.5 μm.

In terms of clogging with leukocytes or increase in the loss of pressure, the average pore size of a non-woven fabric is preferably 2 μm or more. In addition, in terms of ability to capture leukocytes, it is preferably 30 μm or less. The average pore size is more preferably between 2 and 20 μm, and most preferably between 2 and 10 μm.

When a non-woven fabric is used as a filter element, in order to improve capability of removing leukocytes or prevent clogging, two or more types of non-woven fabrics that are different in terms of average fiber diameter, average pore size, weight, or the like, may be used in combination, or at least one type of porous body other than a non-woven fabric having continuous pores in a three-dimensional network state may also be used with the combination of at least one type of non-woven fabric.

When a filter element is filled in a filter holder that is used for a leukocyte removal filter device, the filling density is preferably 0.1 $g/cm^3$ or more, in terms of capability of removing leukocytes. In addition, in terms of clogging with blood cells or increase in the loss of pressure, the filling density is preferably 0.5 $g/cm^3$ or less. It is more preferably between 0.1 and 0.3 $g/cm^3$, and most preferably between 0.15 and 0.25 $g/cm^3$.

With regard to the form of the above filter element, or the form of the first filter constituted with a single (a single slice) filter element or the combined use of several (several slices of) filter elements, any type of form such as a flat membrane (plate) form, a cylindrical form (hollow form), or a bag form can be adopted, as long as it is able to filtrate blood. In terms of handlability, the form of a flat membrane is preferable. In such a case, it is preferable that one or several filter elements be laminated so as to constitute the first filter. When several filter elements are laminated, the filter elements may have the same material, micro structure, average pore size, pore size distribution, and membrane thickness. Moreover, several or all these factors may be different. Furthermore, a single filter element (a single slice) may be uniform in terms of micro structure, average pore size, pore size distribution, etc., or such a single filter element may have an ununiform structure such as a gradient structure.

The size of the first filter is not limited, as long as its capability of removing leukocytes is between 1.0 and 3.5 for 450 $cm^3$ of the hemocyte suspension to be treated. However, if the size is too large, workability decreases in medical sites. In addition, as the holder size of a filter increases, the cost significantly increases on the side of manufacturers. Thus, the effective area of the first filter as a practical value is preferably between 4 and 300 $cm^2$, more preferably between 10 and 250 $cm^2$, and most preferably between 10 and 200 $cm^2$.

The effective area of the first filter means a flat area of a filter portion through which the hemocyte suspension actually passes, from which a filter nipping portion (a portion for fixing the filter to the filter holder) is excluded. Thus, it does not mean an area including the surface of internal pores in the membrane.

For the purpose of sufficiently conducting introduction of a new functional group by the coating method, etc., or immobilization of such a functional group (for the purpose of suppressing elution of a coating material to the minimum during the use), the surface of the filter element may be treated with suitable agents such as acid or alkali, or with plasma or electron beam.

When a non-woven fabric obtained from an organic polymer fiber, a porous material having continuous pores in a three-dimensional network state obtained by the phase separation method, or the like, is used as a first filter, if capability of removing leukocytes between 1.0 and 3.5 for 450 $cm^3$ of the hemocyte suspension to be treated cannot be achieved by the direct use of such a material, the surface portion of the filter element capable of coming into contact with the hemocyte suspension is preferably modified by chemical modification or the like. A known method of introducing a hydrophilic functional group and a nitrogen-containing basic functional group in a well-balanced manner is particularly effective.

The expression "the surface portion of the filter element capable of coming into contact with the hemocyte suspension" does not only mean the front and back sides of a flat membrane, for example, but also includes the surface of internal fine pores existing in the flat membrane. When such a filter element is a non-woven fabric for example, the entire surface of fibers constituting the non-woven fabric (excluding an entangled fiber portion) means the surface portion of a filter element.

A method of introducing a hydrophilic functional group or nitrogen-containing basic functional group into at least the surface portion of a filter element is not particularly limited. Such a method is not particularly limited, as long as it is a method that does not significantly occlude the fine pores of the filter element, or when the surface of the original filter element exhibits non-selective adsorption of blood cell components, a method of uniformly introducing a necessary functional group without exposing the above surface. Examples of such a method may include those described as methods of modifying the surface of the composite porous membrane of the present invention or the surface of a supporting porous membrane constituting it. The coating method is particularly preferable.

In addition, the surface portion of a filter capable of coming into contact with a hemocyte suspension preferably consists of a material that does not affect blood cells. The term "material that does not affect blood cells" is used to mean a material that does not significantly impair the original performance of blood cell components recovered after filtration (mainly, erythrocytes, thrombocytes, or small quantities of leukocytes) by the contact of blood cells with the material during the filtration, or a material that does not excessively activate blood cell components. As such a material, a polymer material having a hydrophilic functional group is adequate. As such a hydrophilic functional group, one or more types can be selected from the aforementioned group of hydrophilic functional groups.

It is preferable, if a material constituting a filter element used as a first filter originally has such a hydrophilic functional group. However, when such a filter element contains no such hydrophilic functional groups, or when it contains a very small amount of hydrophilic functional group and thus it may affect blood cells, it is preferable that a hydrophilic functional group be introduced into at least a surface portion capable of coming into contact with a hemocyte suspension, as necessary, by a suitable method selected from among several surface modification methods as described above. In this case also, the coating method is preferably applied, and a hydrophilic functional group can be introduced by such a method.

Next, the second filter of the leukocyte removal filter device of the present invention will be described.

The second filter is composed of one or more composite porous membranes of the present invention as described above.

The second filter has any form such as a flat membrane form or a cylindrical form, as long as it is able to filtrate blood. The second filter with a flat membrane form is easily handled, and thus it is preferable. When several slices of composite porous membranes are used, the material, opening ratio, average pore diameter, standard deviation of pore diameter, thickness, the structure of an internal membrane, or the like, of a porous membrane constituting each composite porous membrane, may be completely identical. Otherwise, several factors or all factors may differ from one another. In the case of a supporting porous membrane constituting a composite porous membrane also, the material, average pore size, or the like, may be identical, or several or all factors may differ from one another.

It is preferable that the surface portion of the second filter capable of coming into contact with a hemocyte suspension consist of a material that does not affect blood cell components, as in the case of the first filter, or a material that has low affinity for blood cell components and hardly causes non-selective adhesion of blood cell components. (There is a possibility that the composite porous membrane is occluded due to adhesion of blood cells.) As described in the section for the first filter, it has been known that a polymer material with high hydrophilicity is suitable as such a material. Thus, it is preferable that at least the surface portion of a composite porous membrane have one or more types selected from among the aforementioned hydrophilic functional groups.

It is preferable that a material forming a composite porous membrane originally have a hydrophilic functional group. However, when a composite porous membrane contains no such hydrophilic functional groups at least on the surface portion thereof, or when it contains a very small amount of hydrophilic functional group and thus it may affect blood cells, it is preferable that the surface be modified by coating or the like, and that it be then used as a second filter, as described above.

A coating polymer that is to be introduced into at least the surface portion of a composite porous membrane by the coating method is preferably obtained by polymerization (copolymerization) of one or more types selected from among monomer species having a hydrophilic functional group. A nitrogen-containing basic functional group may also be contained in a coating polymer introduced into a composite porous membrane within a range where it does not cause non-selective adsorption of blood cell components, or within a range where it does not affect blood cell components. For such introduction, one or more types of the aforementioned monomer species having a nitrogen-containing basic functional group are preferably used. In terms of the improvement of productivity on the side of manufacturers of filter devices and cost reduction, it is advantageous and preferable that the coating polymer used for the first filter be also used for the second filter.

From the viewpoint of the number of pores in the second filter, clogging with leukocytes, and the amount of a hemocyte suspension to be treated, the effective area of the second filter is 4 cm² or more. Also, from the viewpoint of the size of a filter device and operability in medical sites, the effective area of the second filter is 300 cm² or less. The effective area is preferably between 10 and 200 cm², more preferably between 10 and 150 cm², and most preferably between 10 and 100 cm².

The effective area of the second filter means a flat area of a filter portion through which the hemocyte suspension actually passes, from which a filter nipping portion (a portion for fixing the filter to the filter holder) is excluded. Thus, it does not mean an area including the surface of internal pores in the membrane.

The leukocyte removal filter device of the present invention is a filter device having a first filter located on the entrance side of a hemocyte suspension and a second filter located on the exit side thereof. Basically, the leukocyte removal filter device may have any structure, as long as it is constructed such that a whole hemocyte suspension passed through the first filter is successively filtrated through the second filter. When the second filter is established on the hemocyte suspension entrance side, there are cases where a composite porous membrane may be occluded with large quantities of leukocytes.

It is also possible that each of the first and second filters be filled in a different filter holder, and both holders be connected using a tube or the like and be used (division type). In this case, this structure is characterized in that the form and size of both filters of the present invention can be determined independently. For example, if the effective area of the second filter is determined to be 2 times larger than that of the first filter, the clogging of the second filter hardly occurs, and thus it becomes possible to reduce the volume of a filter element of the first filter.

It is also possible to fill the first and second filters in a single filter holder and use it (integral type). In the case of such an integral type, since only one filter holder is used, it is preferable in terms of production cost. In addition, the form of a filter holder is devised in various ways, so that the same effects as those of the aforementioned division type can be obtained.

Practically, an integral-type structure wherein the flat membrane-type first filter (which is, for example, obtained by laminating several non-woven fabrics) is overlaid on the second filter formed by laminating one or more slices of composite porous membranes of the same size and wherein the obtained filter is filled in a simple form of filter holder is preferably used in terms of operability in medical sites and production cost.

Figure 5:
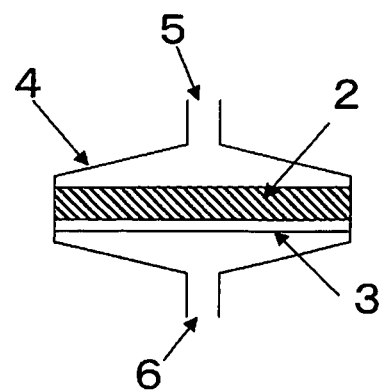
FIG. 5 is a conceptual diagram showing an integral-type leukocyte removal filter device.

FIG. 5 is a conceptional view showing the basic structure of an integral-type leukocyte removal filter device. This leukocyte removal filter device basically consists of a first filter (2), a second filter (3), a filter holder (4), a hemocyte suspension entrance (5), and a filtrated hemocyte suspension exit (6). In this conceptional view, the first filter is conveniently disposed apart from the second filter to clearly explain them in the drawing. However, in an actual situation, both filters are laminated (attached) to each other, and they are filled in a filter holder. Moreover, in the filter holder shown in FIG. 5, as a matter of convenience for expression with the drawing, there are many spaces, which do not exist in the actual filter element. However, such spaces result in the loss of a hemocyte suspension, and thus they do not exist actually.

In addition, when a composite porous membrane used as a second filter consists of a single porous membrane and a single supporting porous membrane, it is preferable that the second filter (composite porous membrane) be disposed in the filter holder, so that the porous membrane face can be located on the hemocyte suspension entrance side. If the second filter is disposed such that the supporting porous membrane face is located on the hemocyte suspension entrance side, filtration resistance increases, and thus filtration efficiency may significantly decrease.

The capability of the leukocyte removal filter device of the present invention to remove leukocytes is preferably 4.0 or more, more preferably 4.5 or more, and most preferably 5.0 or more, for 450 cm³ of the hemocyte suspension to be treated. If such capability of removing leukocytes is less than 4.0, side effects caused by residual leukocytes occur at high probability during blood transfusion. In order to achieve a significant effect of reducing the volume of a filter element of the leukocyte removal filter device, the capability of removing leukocytes is preferably 8.0 or less.

The volume of filter element V (the volume of filter element consisting of the first filter volume and the second filter volume) of the leukocyte removal filter device is between 2 and 18 cm³, preferably between 2 and 15 cm³, more preferably between 3 and 12 cm³, and most preferably between 3 and 10 cm³. If such a volume of filter element is less than 2 cm³, the capability of the first filter of removing leukocytes becomes insufficient. In contrast, if such a volume of filter element exceeds 18 cm³, the effect of reducing a filter element decreases, and as a result, the effect of reducing the loss of a hemocyte suspension also decreases.

The volume of filter element V (cm³) means the void volume of a filter element. The value V can be obtained by filling a filter holder containing a filter element with a hemocyte suspension or an alternative liquid such as a normal saline solution and then actually measuring the volume (cm³) of the liquid filled in the filter holder.

With regard to the leukocyte removal filter device of the present invention, when the supporting porous membrane of a composite porous membrane used as a second filter is made from the same material as that of a first filter, and also when the amount of a porous membrane used of a composite porous membrane is substantially negligible when compared with that of the first filter, the value calculated using the following formula (2) can be used as such V.

$$V = Wf[(1/d) - (1/\rho)] \quad (2)$$

Herein, d (g/cm³) represents the filling density of the total filter element consisting of the first filter and the second filter that are filled in the filter holder; Wf (g) represents the weights of the first and second filters filled therein; and ρ (g/cm³) represents the density of a material forming the first filter and the supporting porous membrane of the second filter (composite porous membrane). For example, when the first filter and the supporting porous membrane are non-woven fabrics made from polyethylene terephthalate, ρ is approximately 1.3.

The cell culture diaphragm of the present invention will be described.

The cell culture diaphragm of the present invention is used to divide different cell groups in a cell culture solution in a state where they are allowed to come into contact with each other, so as to co-culture the cells. It is a cell culture diaphragm using the composite porous membrane of the present invention.

In the present invention, the term "co-culture of cells" is used to include not only the simultaneous growth of two or more types of cell groups in a cell culture solution, but also include a case where the growth and/or differentiation of at least one type of cells is promoted by contact with cell groups that are different from each other, and a case where at least one type of cells is allowed to grow in number, while suppressing the differentiation thereof.

When cells are cultured using the cell culture diaphragm of the present invention, the cell culture diaphragm is disposed in a cell culture solution. Depending on the number and form of the diaphragm, at least two culture regions separated by the diaphragm of the present invention are obtained. In such at least two culture regions adjacent to each other, different types of cells are co-cultured. For example, two cell culture diaphragms, each of which is cut into a square of the same size, are laminated such that the supporting porous membranes thereof (for example, non-woven fabrics) are located inward, and 3 sides thereof are then sealed by heat sealing, so as to obtain a bag-form diaphragm sheet. Such a diaphragm sheet is disposed in a cell culture solution (the opening portion of the bag is exposed from the liquid face, or it is closed). Thus, two culture regions adjacent to each other that are separated by a porous membrane can be obtained inside and outside the bag-form diaphragm sheet (inside and outside the bag). As a result, cells can be co-cultured in the two culture regions that are located inside and outside. Likewise, if two bag-form diaphragm sheets are disposed in a cell culture solution, three culture regions separated by a porous membrane can be obtained. Further, if three bag-form diaphragm sheets are disposed therein, four culture regions can be obtained. Moreover, for example, when such a cell culture diaphragm is adhered to one end face of a glass tube to prepare an integrated cup-type container, and when such an integrated cup-type container is placed in a well of a culture plate, two culture regions can be obtained inside and outside the cup in the well.

That is to say, different cell groups are co-cultured in at least two culture regions adjacent to each other that are separated by a porous membrane, and further, the average pore size of a supporting porous membrane and that of a porous membrane are adjusted depending on the size of the cell to be cultured, so as to conduct the co-culture of cells enabling effective intracellular contact.

Since the cell culture diaphragm of the present invention can be processed into a desired form, the separation and recovery of grown cells of interest can be extremely easily carried out. For example, in the case of co-culture using the aforementioned bag-form diaphragm sheet, when cells of interest have been allowed to grow outside the bag-form sheet, the cells of interest can be easily separated and recovered only by removing the bag-form diaphragm sheet from the culture solution. Moreover, in the case of co-culture using the aforementioned cup-type culture apparatus for example, even if cells of interest have been allowed to grow inside the cup, they can be easily separated and recovered. (Naturally, pipetting or a centrifugal operation is required, as necessary.)

According to the cell culture process of the present invention, at least two types of cell groups are divided in a cell culture solution in a state where they are allowed to come into contact with each other, and then co-cultured. The combination of cell groups to be co-cultured is not limited. The combination of cell groups, the contact with which affects the growth or differentiation of at least one type of cells, is preferable. The combination of cell groups, which are come into contact with each other, thereby promoting the growth and/or differentiation of at least one type of cells, or thereby promoting only the growth in number while suppressing differentiation, is particularly preferable.

Examples of such a combination of cell groups may include: the combination of "a hematopoietic stem cell group with a mouse bone marrow-derived stromal cell group;" and the combination of "a hematopoietic stem cell group with a human vascular endothelial cell group," which preferentially promotes only the growth in number of the hematopoietic stem cells due to intracellular contact in a state where the cells are undifferentiated. As a cell group of interest that is allowed to grow by intracellular contact, a hematopoietic stem cell group is preferable because the application thereof to various types of regenerative medicine has been studied and also because there is a possibility that the above cell group is utilized in cultured blood business.

The surface of the cell culture diaphragm of the present invention may be modified by a hydrophilic treatment or the like, as described in the production process of a composite porous membrane and its supporting porous membrane.

A process of modifying the surface of the cell culture diaphragm is not limited. As in the case of the composite porous membrane or supporting porous membrane, the coating method is preferable. The surface modification of the cell culture diaphragm can be carried out for the purpose of suppressing cellular adhesiveness, or to the opposite, for the purpose of imparting such cellular adhesiveness. When the coating method is applied, examples of a coating polymer used herein may include the aforementioned hydrophilic polymers such as collagen, fibronectin, vitronectin, proteoglycan, or glycosaminoglycan, and conventionally known biocompatible polymers such as gelatin, lectin, or polylysine. These polymers can be used singly or in combination of two or more types.

Measurement methods used in the present invention will be described below.

(1) Average Pore Diameter D, Standard Deviation of Pore Diameter σd, Opening Ratio, and the Percentage of Through-Pores of Porous Membrane, Honeycomb-Structured Thin Porous Membrane, and Etched Membrane of Composite Porous Membrane The average pore diameter D, standard deviation of pore diameter σd, opening ratio, and the percentage of through-pores of a porous membrane can be measured by taking an optical- or scanning electron-photomicrograph from the direction vertical to the membrane flat surface of the porous membrane, picking up the pore group (through-pores and non-through pores) of the porous membrane observed on the obtained planar image (photograph) using image analyze software Image-Pro Plus (manufactured by Media Cybernetics, Version 4.0 for Windows (registered trade mark)), and analyzing the obtained image.

Specifically, the obtained composite porous membrane is cut from the periphery of the center into a square with a side of 6.7 cm. The center thereof is defined as point A, and the 4 angles thereof are defined as B', C', D', and E'. In addition, 4 midpoints between point A and each of the above 4 angles are defined as B, C, D, and E. Thereafter, the peripheral portions of these 9 points is photographed with a scanning electron microscope (S-3000N, manufactured by Hitachi Ltd.) from the direction vertical to the membrane face on the side to which the porous membrane has been adhered (1,000 to 3,000-fold).

The thus obtained 9 photographs are incorporated into image analysis software. An image range including approximately 200 pores is arbitrarily selected from each photograph, and the image contrast is then fully adjusted, such that it can be analyzed. The dark region (pore region) is automatically extracted. Moreover, from among the thus extracted dark regions, those clearly differing from pore portions are manually eliminated. Thereafter, the average pore diameter of pores contained in each of the selected 9 is calculated. Subsequently, the values of 9 photographs are averaged, so as to obtain "average pore diameter D."

The term "standard deviation of pore diameter σd" is used to mean a value obtained by further averaging the standard deviations of pore diameters in the 9 image ranges, whose "average pore diameter D" has been determined as described above. The term "opening ratio" is used to mean a value that is obtained by averaging 9 values of opening ratio obtained in the same above image ranges.

In each of the 9 image regions, whose D, σd, and opening ratio are calculated as described above, the total number of pores contained in each photograph is indicated with N1, and the number of through-pores in the total number is indicated with N2. Both types of pores are counted, and the value obtained by the formula $N2/N1 \times 100(\%)$ is calculated. The percentage of through-pores is calculated as a mean value of the thus obtained 9 values.

The average pore diameter D, standard deviation of pore diameter σd, and opening ratio of a honeycomb-structured thin porous membrane, and those of an etched membrane, are measured and calculated in the same above manner. However, such a honeycomb-structured thin porous membrane or etched membrane does not have a supporting porous membrane. Accordingly, with regard to the honeycomb-structured thin porous membrane, through-pores are defined as pores, through which a disciform specimen holder or a tape used for adhesion to the specimen holder can be observed. Thus, the ratio of such through pores is calculated. In addition, with regard to the etched membrane, since it has a high membrane thickness, it has been difficult to observe the structure of adhesion face through pores. Thus, from the viewpoint of production process thereof, it is assumed that pores are all through-pores.

(2) Process of Measuring Average Membrane Thickness T and Standard Deviation of Membrane Thickness σt of Porous Membrane of Composite Porous Membrane, Honeycomb-Structured Thin Porous Membrane, and Etched Membrane, and Observation of Sectional Structure A composite porous membrane is gently adhered and fixed to a disciform specimen holder of a scanning electron microscope, using a two-sided tape. Thereafter, the porous membrane is coated with platinum via evaporation. (The thickness of the membrane coated via evaporation was set at approximately 12 nm.) Thereafter, this membrane is observed under a scanning electron microscope (S-3000N, manufactured by Hitachi Ltd.), a photograph of a membrane section is then taken from the direction immediately lateral to the membrane (membrane flat surface direction). Thereafter, the average membrane thickness T of a composite porous membrane and that of a porous membrane constituting it are measured from the membrane section in this photograph based on the scale described therein.

Specifically, the sections near the 9 points (A to E and B' to E'), which have been selected for the calculation of the average pore diameter D in (1) above, are observed under a scanning microscope, and the membrane thickness is then calculated at intervals of 50 μm, using the scale in the image. Such membrane thickness is measured at approximately 100 points in each of the 9 points. When 100 points cannot be observed in a scanning electron microscope sample, several samples are prepared from the periphery of the same point, so that the points to be observed can be increased. The average membrane thickness of each of the 9 points is calculated from the thus obtained membrane thickness. Subsequently, the average membrane thicknesses of the 9 points are averaged, so as to calculate an "average membrane thickness T."

The honeycomb-structured thin porous membrane and the etched membrane are also observed in the same manner.

As with a pre-treatment performed before observation under a scanning electron microscope, a sample used for cross-sectional observation is prepared by immersing in ethanol, freezing with a liquid nitrogen, and then cutting it.

(3) Measurement of Average Pore Size of Non-Woven Fabric

An average pore size is evaluated in accordance with the bubble point method described in ASTM-F316-86, using Automated Perm Porometer (registered trade mark) (manufactured by Porous Materials, Inc.). For the measurement, a liquid being suitable for sufficiently wetting the inside of pores of the non-woven fabric is used.

(4) Adhesion Test

A composite porous membrane is cut into a square with a size of 10 mm×10 mm, and this square is used as a test piece. This test piece is placed in a 50-ml beaker filled with 50 ml of water, and it is immersed therein for 30 minutes. Thereafter, a stirrer bar with a length of 25 mm (maximum diameter: 8 mm) is placed therein, and the water is then stirred at a rate of 200 rpm for 30 minutes. Thus, it is observed whether or not a supporting porous membrane is removed from a porous membrane. A case where the supporting porous membrane is not removed from the porous membrane is represented by an open circle, and a case where it is removed therefrom is represented by a cross.

(5) Simple Tensile Test

A composite porous membrane, honeycomb-structured thin porous membrane (Comparative example 1) or an etched membrane (Comparative example 4) is cut into a piece with a size of 15×25 mm, and this piece is used as a test piece. The points that are 5 mm from both ends (short side portions) of each test piece are nipped with BINDER CLIPS (registered trade mark) (No. 107, manufactured by LION). Thereafter, one point is fixed, so as to suspend the membrane in the vertical direction. A weight of 30 g or 50 g is attached to the other clip, and it is then observed whether or not the composite porous membrane, honeycomb-structured thin porous membrane or etched membrane is broken. A case where such a membrane is not broken even with a weight of 50 g (tensile strength: 50 g or more) is evaluated as an open circle, and a case where such a membrane is broken with a weight of 30 g (tensile strength: less than 30 g) is evaluated as a cross.

(6) Water Permeation Test

Composite porous membranes that have been punched into 25 mmφ (Examples 1 to 4), membrane sections obtained by overlaying a honeycomb-structured thin porous membrane on the supporting porous membrane (that is a coated-nonwoven fabric in the present example) of a composite porous membrane whose water permeability is to be compared and then punching out it into a round of 25 mmϕ (Comparative examples 1 and 2), and an etched membrane (Comparative example 4) punched into a round of 25 mmϕ, are prepared. The thus prepared membranes are set into a commercially available filter holder (Swin-Lok™ Filter Holder, manufactured by CORNING), so as to conduct a water permeation test. In the case of the composite porous membrane and the membrane obtained by overlaying a honeycomb-structured thin porous membrane on a supporting porous membrane, it is set such that the porous membrane or honeycomb-structured thin porous membrane is disposed on the water entrance side of the filter holder.

As such a water permeation test, a 50-ml disposable syringe (manufactured by Terumo Corp.) is connected with the aforementioned water entrance side of the filter holder, and it is vertically erected. Thereafter, a filter sample is moistened with approximately 1 ml of ethanol. Thereafter, the disposable syringe is filled with distilled water, and the time required for the distilled water to freely fall from a syringe scale of 60 ml to 30 ml is then measured, thereby calculating the amount of water permeated per filter unit area and per unit time.

(7) Simple Hemocyte Suspension Permeation Test

A composite porous membrane or etched membrane (Comparative example 4) that has been punched into a round of 25 mmϕ is set in a commercially available filter holder (Swin-Lok™ Filter Holder, manufactured by CORNING), so as to conduct a hemocyte suspension permeation test. In the case of a composite porous membrane, it is set such that the porous membrane is disposed on the hemocyte suspension entrance side of the filter holder.

The hemocyte suspension used herein is obtained by previously removing leukocytes from fresh human whole blood using a coated non-woven fabric or the like, so as to reduce the concentration of leukocytes contained therein to 1/630.

A 10-ml disposable syringe (manufactured by Terumo Corp.) is connected with the aforementioned hemocyte suspension entrance side of the filter holder, and it is vertically erected. Thereafter, the disposable syringe is filled with the hemocyte suspension up to the scale of 5 ml, and the time required for the hemocyte suspension to freely fall from a syringe scale of 5 ml to 3 ml is then measured. The time required for permeation of 2 ml of the hemocyte suspension is evaluated.

Such "fresh human whole blood" is prepared by adding, as an anticoagulant, 14 cm$^3$ of a filtrated CPD solution (a solution obtained by dissolving 26.3 g of trisodium citrate dihydrate, 3.27 g of citric acid monohydrate, 23.2 g of glucose, and 2.51 g of sodium dihydrogen phosphate dihydrate, in 1 L of distilled water used for injection, and then filtrating it through a filter with a pore size of 0.2 μm) to 100 cm$^3$ of collected blood, mixing them, and conserving the mixture at 20° C. for 3 hours.

(8) Evaluation of Capability of Removing Leukocytes

An integral-type filter structure as shown in FIG. 5 is evaluated.

Such capability of removing leukocytes is evaluated by passing 450 cm$^3$ of fresh human whole blood through a filter device at a constant flow rate of 25 cm$^3$/min., using a syringe pump, collecting a certain amount of blood from all the whole blood recovered before and after filtration, and measuring the concentration of leukocytes with a residual leukocyte measurement reagent system, LeucoCOUNT™ kit, a flow cytometer FACS Calibur, and analysis software CELL Quest (all of which are manufactured by BD Bioscience, U.S.A).

The aforementioned blood filtration experiment was carried out twice. The values are obtained using the following formula (1). A mean value of such values is defined as the value of such capability of removing leukocytes.

Capability of removing leukocytes=−log(the concentration of leukocytes after filtration of a hemocyte suspension/the concentration of leukocytes before filtration thereof)    (1)

(9) Calculation of Volume of Filter Element (V)

In the case of leukocyte removal filter devices used in Examples and Comparative examples, the supporting membrane of a composite porous membrane used as a second filter is made from the same material as that of a first filter. In addition, when compared with the first filter, the used amount of the porous membrane used of such a composite porous membrane is substantially negligible. Thus, V is calculated using the following formula (2).

$$V = Wf[(1/d)-(1/\rho)] \quad (2)$$

Herein, d (g/cm$^3$) represents the filling density of the total filter element that is filled in the filter holder; Wf (g) represents the weights of the first and second filters filled therein; and ρ (g/cm$^3$) represents the density of a material forming the first filter and the supporting porous membrane of the second filter (composite porous membrane). For example, when the first filter and the supporting porous membrane are non-woven fabrics made from polyethylene terephthalate, ρ is approximately 1.3.

EXAMPLES

The present invention will be described in detail in the following examples and comparative examples. However, these examples are not intended to limit the scope of the present invention.

Example 1

1. Production of Coated Non-Woven Fabric Piece 1-1. Synthesis of Coating Polymer Synthesis of 2-hydroxyethyl methacrylate (HEMA)/2-(dimethylamino)ethyl methacrylate (DMAMA) random copolymer 126 g (0.970 mol) of 2-hydroxyethyl methacrylate (HEMA, manufactured by Mitsubishi Rayon Co., Ltd.), 4.72 g (0.030 mol) of 2-(dimethylamino)ethyl methacrylate (DMAMA, manufactured by Wako Pure Chemical Industries, Co., Ltd.), and 460 g of ethanol were placed in a separable flask (capacity: 1 L). Thereafter, oxygen was removed by nitrogen bubbling, and the temperature of the reaction system was then increased to 60° C., while maintaining the inside of the container in a nitrogen atmosphere. Thereafter, a deoxidized ethanol solution (ethanol: 40.0 g), in which 0.822 g (5.01 mol) of azobisisobutyronitrile (AIBN, manufactured by Wako Pure Chemical Industries, Co., Ltd.) had been dissolved, was added dropwise to the above reaction system over approximately 1 hour. The obtained mixture was continuously stirred at 60° C., and 225 minutes after initiation of the addition of AIBN, p-methoxyphenol (manufactured by Wako Pure Chemical Industries, Co., Ltd.) was added to the reaction solution, so as to terminate the polymerization reaction. Thereafter, n-hexane was added bit by bit to the obtained reaction solution, so as to precipitate a polymer. The polymer was taken out by decantation. Thereafter, dissolution in ethanol and reprecipitation operation using n-hexane were repeated several times, so as to purify the polymer.

After such purification, the yield of the polymer (with respect to the amount of the monomers added) was found to be 72 wt %. The number average molecular weight (Mn) of the polymer obtained by GPC measurement (relative to standard polystyrene) was found to be $1.2 \times 10^5$, and the weight average molecular weight thereof (Mw) was found to be $4.1 \times 10^5$. Thus, Mw/Mn was found to be 3.4. In addition, the copolymerization composition ratio in the polymer, which was calculated based on the measurement of the amount of monomer residue by gas chromatography (GC) performed on the reaction solution after completion of the polymerization, was found to be HEMA/DMAMA=97/3 (molar ratio).

1-2. Coating of Non-Woven Fabric with Coating Polymer (HEMA/DMAMA (97/3 (Molar Ratio)) Copolymer)

An ethanol solution containing 1.0 wt % of the HEMA/DMAMA (97/3 molar ratio) copolymer obtained in 1-1. above was prepared. The thus prepared solution was used as a coating solution. A polyethylene terephthalate non-woven fabric (manufactured by Asahi Kasei Corp.; Microweb) having an average fiber diameter of 1.2 μm, an average pore size of 6.3 μm, and a mass per unit area of 40 g/m² (fiber weight for 1 m² of non-woven fabric), and a thickness of 0.2 mm, was selected as a non-woven fabric to be used herein. This non-woven fabric was continuously immersed in a coating solution for an immersion time of 5 seconds. Thereafter, the non-woven fabric was nipped with a nip roll and passed through it, so as to remove an excess coating solution. Thereafter, the resultant was dried, so to as obtain a coated non-woven fabric.

2. Production of Composite Porous Membrane

Using chloroform as a solvent, there was prepared a 1 g/L hydrophobic organic solvent solution containing, as solutes, poly-ε-caprolactone (PCL) (manufactured by Wako Pure Chemical Industries, Co., Ltd.; average molecular weight: 70,000 to 100,000) and a polyacrylamide amphipathic polymer (represented by the aforementioned structural formula (1)). The weight ratio of PCL/polyacrylamide amphipathic polymer was 9/1.

The polyacrylamide amphipathic polymer represented by the chemical formula (1) was a random copolymer, wherein the molar ratio between unit m and unit n was m/n=4/1.

The polyacrylamide amphipathic polymer was produced by subjecting dodecyl acryloylamide ($CH_2$=CH—CONH—$C_{11}H_{22}$—$CH_3$) (A mole) and 6-acrylamide hexanoic acid ($CH_2$=CH—CONH—$C_5H_{10}$—COOH) (B mole) at a molar ratio of A/B=4/1 to a radical polymerization method using AIBN as an initiator in benzene (monomer concentration: 6 wt %; polymerization temperature: 60° C.). The weight average molecular weight Mw of the obtained amphipathic polymer was found to be $2.5 \times 10^4$ (GPC method; relative to standard polystyrene).

6-acrylamide hexanoic acid was synthesized by subjecting acryloyl chloride (manufactured by Aldrich) and 6-aminohexanoic acid (manufactured by Aldrich) to a dehydrochlorination reaction at 0° C. in an aqueous solvent. Dodecyl acryloylamide was synthesized by subjecting acryloyl chloride and dodecylamine (manufactured by Aldrich) to a dehydrochlorination reaction at 0° C. in a chloroform solvent.

Subsequently, a coated non-woven fabric piece prepared in 1-2. above was cut into a square with a side of 16 cm. Thereafter, the non-woven fabric was immersed in pure water in a beaker, and deaeration was then carried out using an ultrasonic cleaner for 5 minutes, so that the non-woven fabric was allowed to sufficiently retain water. The thus obtained non-woven fabric retaining a sufficient amount of water (hydrous non-woven fabric) was removed from the beaker and then placed on a glass plate. Thereafter, a metal frame with a thickness of 1 mm that had been punched into a square with a side of 15 cm was disposed on the non-woven fabric, such that the hydrous non-woven fabric was exposed from the whole area of the punched portion of the metal frame. Thus, the glass plate, the hydrous non-woven fabric, and the metal frame were laminated, and the resultant was fixed with a clip.

Thereafter, 14 cm³ of the prepared chloroform solution containing PCL and a polyacrylamide amphipathic polymer was gently poured into the punched portion of the metal frame, from which the hydrous non-woven fabric was exposed. Thereafter, air with a relative humidity of 60% was blown at an amount of 6 L/min to the surface of the above solution in a thermo-hygrostat with a room temperature of 25° C. and a relative humidity of 40%, so as to remove chloroform, thereby forming a porous membrane containing PCL as a main component on the hydrous non-woven fabric. Subsequently, the metal frame was removed, and the non-woven fabric was subjected to air drying at room temperature, so as to obtain a composite porous membrane. The obtained composite porous membrane had a membrane thickness of approximately 240 μm. The opening ratio, D, σd/D, the percentage of through-pores, T, and σt/T are as shown in Table 1.

The scanning electron photomicrographs obtained by photographing the surface of the obtained composite porous membrane from the porous membrane side are shown in FIG. 1 (1,000-fold) and FIG. 2 (3,000-fold). The structure of the non-woven fabric that is a supporting porous membrane could be observed through pores of the porous membrane. In addition, a state where fibers constituting the non-woven fabric penetrated into the porous membrane and where as a result, pores are partially occluded therewith, could also be observed on the surface of the porous membrane.

Figure 3:
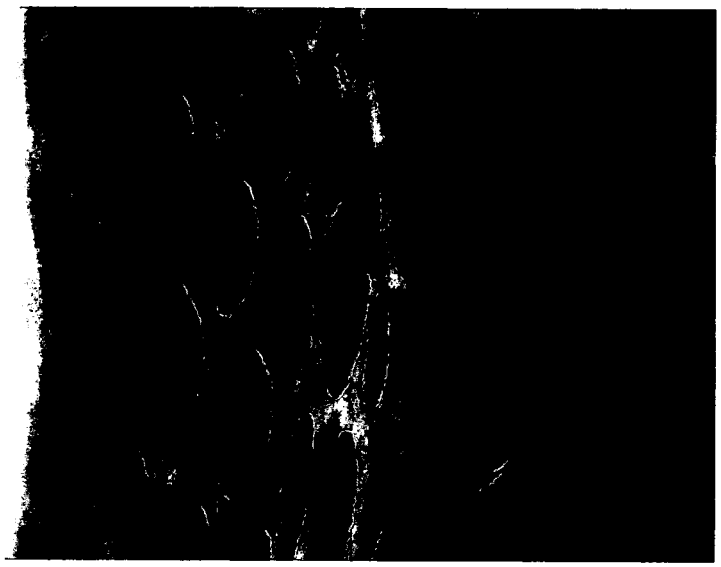
FIG. 3 is a scanning electron photomicrograph (3,000-fold) showing the section of a composite porous membrane obtained in Example 1.

Moreover, a scanning electron photomicrograph showing the section of the composite porous membrane is shown in FIG. 3 (3,000-fold). It could be observed that each pore had a structure as a spherical through-pore which swelled in the porous membrane, and that pores adjacent to one another were communicated with one another.

An adhesion test was carried out. As a result, it was found that the porous membrane was not separated from the supporting porous membrane.

In addition, a simple tensile test was also carried out. As a result, it was found that a test piece was not broken with a force of 50 g. No cracks were observed on the porous membrane.

A water permeation test was carried out using pure water. The result was found to be 17.6 ml/cm²/min.

The obtained composite porous membrane was immersed in a solution containing 0.1 wt % of the HEMA/DMAMA (97/3 (molar ratio)) copolymer synthesized in 1-1. above (solvent: ethanol) for 10 seconds for coating. After completion of the immersion, the membrane was fully dried, so as to obtain a coated composite porous membrane.

The coated composite porous membrane was subjected to a simple permeation test using a hemocyte suspension. As a result, the period of time required for permeation of 2 ml of the hemocyte suspension was found to be 30 seconds. When compared with the result obtained in Comparative example 4 described later, this was a good permeation rate.

Example 2

A composite porous membrane was produced in the same manner as in the section 2 of Example 1 with the exception that dichloromethane was used instead of chloroform as a solvent for the used hydrophobic organic solvent solution.

The opening ratio, D, σd/D, the percentage of through-pores, T, and σt/T of the porous membrane of the obtained composite porous membrane are as shown in Table 1.

An adhesion test was carried out. As a result, it was found that the porous membrane was not separated from the supporting porous membrane.

A simple tensile test was also carried out. As a result, it was found that a test piece was not broken with a force of 50 g. In addition, no cracks were observed on the porous membrane.

A water permeation test was carried out using pure water. The result was found to be 15.4 ml/cm$^2$/min.

Example 3

A composite porous membrane was produced in the same manner as in the section 2 of Example 1 with the exception that polysulfone (PSU: manufactured by Teijin Acomo Engineering Plastics, UDEL P-3500) was used instead of PCL as a solute for the used hydrophobic organic solvent solution.

The opening ratio, D, σd/D, the percentage of through-pores, T, and σt/T of the porous membrane of the obtained composite porous membrane are as shown in Table 1.

An adhesion test was carried out. As a result, it was found that the porous membrane was not separated from the supporting porous membrane.

A simple tensile test was also carried out. As a result, it was found that a test piece was not broken with a force of 50 g. In addition, no cracks were observed on the porous membrane.

A water permeation test was carried out using pure water. The result was found to be 14.2 ml/cm$^2$/min.

Example 4

A composite porous membrane was produced in the same manner as in the section 2 of Example 1 with the exceptions that PSU was used instead of PCL as a solute for the used hydrophobic organic solvent solution, that a polymer (concentration: 4 g/L; liquid amount: 21 cm$^3$) was casted, and that chloroform was removed in a thermo-hygrostat with a room temperature of 28° C. and a relative humidity of 43%.

The opening ratio, D, σd/D, the percentage of through-pores, T, and σt/T of the porous membrane of the obtained composite porous membrane are as shown in Table 1.

An adhesion test was carried out. As a result, it was found that the porous membrane was not separated from the supporting porous membrane.

A simple tensile test was also carried out. As a result, it was found that a test piece was not broken with a force of 50 g. In addition, no cracks were observed on the porous membrane.

A water permeation test was carried out using pure water. The result was found to be 19.6 ml/cm$^2$/min.

Comparative Example 1

A honeycomb-structured thin porous membrane was formed in the same manner as in section 2 of Example 1 with the exception that 11 cm$^3$ of a hydrophobic organic solvent solution was directly poured into a round glass Petri dish with a diameter of 15 cm without using a coated non-woven fabric. A thin porous membrane formed on the Petri dish was peeled by addition of ethanol. Thereafter, it was attached to and fixed on a ring-shaped supporting frame, and it was then removed.

The opening ratio, D, σd/D, the percentage of through-pores, T, and σt/T of the obtained honeycomb-structured thin porous membrane are as shown in Table 1.

A water permeation test was carried out using pure water. The result was found to be 18.9 ml/cm$^2$/min.

In addition, a simple tensile test was also carried out. As a result, it was found that a test piece was broken only with a force of 30 g. Thus, it was revealed that this membrane did not have practical strength.

Comparative Example 2

A honeycomb-structured thin porous membrane was produced in the same manner as in Example 4 with the exception that 11 cm$^3$ of a hydrophobic organic solvent solution was directly poured into a round glass Petri dish with a diameter of 15 cm without using a coated non-woven fabric.

The opening ratio, D, σd/D, the percentage of through-pores, T, and σt/T of the obtained honeycomb-structured thin porous membrane are as shown in Table 1.

A water permeation test was carried out using pure water. The result was found to be 20.1 ml/cm$^2$/min.

In addition, a simple tensile test was also carried out. As a result, it was found that a test piece was broken only with a force of 30 g. Thus, it was revealed that this membrane did not have practical strength.

Comparative Example 3

A composite porous membrane was produced in the same manner as in Example 4 with the exception that 17 ml of a hydrophobic organic solvent solution was casted in a dry state without impregnating the coated non-woven fabric with water.

A scanning electron photomicrograph of the obtained composite porous membrane showed that cast solution-derived PSU penetrated into the supporting membrane and that several pores of the supporting membrane were thereby occluded. In addition, several honeycomb-state pores were observed on the PSU portion on the side to which air was blown on the composite porous membrane. However, in a majority of pores, the non-woven fabric was exposed, or pores were broken or clogged. Thus, differing from Examples 1 to 4, a smooth porous membrane with high pore size uniformity was not found. Accordingly, it was difficult to determine the opening ratio, D, σd/D, the percentage of through-pores, T, and σt/T of the obtained composite porous membrane.

Comparative Example 4

A pure water permeation test was carried out using an etched membrane made from polycarbonate (PC) (manufactured by MILLIPORE; Isopore Membrane Filter). The result was found to be 12.0 ml/cm$^2$/min.

In addition, the etched membrane was coated with a HEMA/DMAMA (97/3 (molar ratio)) copolymer in the same manner as in Example 1, and a simple hemocyte suspension permeation test was carried out. The result was found to be 57 seconds.

A simple tensile test was also carried out. As a result, it was found that a test piece was not broken with a force of 50 g. Moreover, no cracks were observed.

The opening ratio, D, σd/D, the percentage of through-pores, T, and σt/T of this etched membrane made from PC are as shown in Table 1. Since this membrane had a high thickness, the percentage of through-pores could not be confirmed by observation from the membrane flat surface. However, taking into consideration its production method, it was assumed to be almost 100%. Furthermore, the shape of a pore on the membrane section was cylindrical.

Example 5

1. Production of Leukocyte Removal Device 1-1. Evaluation of Capability of First Filter of Removing Leukocytes Sixteen slices of square non-woven fabrics were cut out of the coated non-woven fabric piece produced in the process described in the section 1-2 of Example 1, such that the effective area of a filter could be 45 cm$^2$ when it was filled in a filter holder. (The effective size of the filter was 6.7 cm×6.7 cm.) The thus obtained sixteen slices were filled in a filter holder, resulting in a filling density of 0.23 g/cm$^3$. Thereafter, a filtration experiment was carried out twice, and 450 cm$^3$ of fresh human whole blood was passed through this filter. As a result, the mean value of the capability of the first filter of removing leukocytes was found to be 2.8.

1-2. Production of Integral-Type Leukocyte Removal Filter Device and Evaluation of Capability Thereof of Removing Leukocytes Sixteen slices of square samples were cut out of any given positions of the coated non-woven fabric piece produced in the section 1-2 of Example 1, such that the effective filter size could be 6.7 cm×6.7 cm. (The effective filter area was 45 cm$^2$.) Such sixteen slices were laminated, so as to produce a first filter.

Subsequently, a single slice of square sample of the same size as that of the first filter was cut out of the center of the coated composite porous membrane obtained in section 2 of Example 1, and this was used as a second filter. (The effective area of the second filter was 45 cm$^2$.) The first filter was overlaid on the second filter, and the thus overlaid filters were filled into a filter holder, such that the entire filter element had a filling density of 0.23 g/cm$^3$, thereby constituting an integral-type leukocyte removal filter device. The first filter was disposed on the entrance side of a hemocyte suspension to be treated, and the second filter was disposed on the exit side of the treated blood.

Such a filling density of 0.23 g/cm$^3$ was considered to be the same as those of the supporting membranes of the first and second filters. Defining Wf as the weight of 17 slices of square non-woven fabrics, the aforementioned formula (2) was used for calculation. As a result, volume of filter element V was found to be 12 cm$^3$.

Thereafter, 450 cm$^3$ of fresh human whole blood was passed through this integral-type leukocyte removal filter device, so as to measure the capability of the device of removing leukocytes. A blood filtration experiment was carried out twice. As a result, the mean value of the capability of removing leukocytes was found to be 4.3.

The above results are shown in Table 2. When compared with Comparative example 5 described later, although almost the same value was maintained as capability of removing leukocytes, the volume of a filter element was significantly reduced. Thus, it was found that a leukocyte removal filter device capable of significantly reducing the loss of a hemocyte suspension could be obtained.

Example 6

A leukocyte removal filter device was produced in the same manner as in Example 6 with the exceptions that two slices of the coated composite porous membranes obtained in section 2 of Example 1 were used as a second filter, and that fifteen slices of the coated non-woven fabrics produced in section 1-2 of Example 1 were used as a first filter.

In this case also, the filling density of the entire filter element was 0.23 g/cm$^3$. Thus, the volume of the filter element was 12 cm$^3$ (the first filter+two slices of supporting membranes).

Thereafter, 450 cm$^3$ of fresh human whole blood was passed through this integral-type leukocyte removal filter device, so as to measure the capability of removing leukocytes thereof. A blood filtration experiment was carried out twice. As a result the mean value of the capability of removing leukocytes was found to be 4.5.

These results are shown in Table 2.

Example 7

The composite porous membrane obtained in Example 2 was immersed in a solution containing 0.1 wt % of a HEMA/DMAMA (97/3 (molar ratio)) copolymer (solvent: ethanol) for 10 seconds, and it was then removed therefrom, followed by drying. Thus, the composite porous membrane was coated with the above solution, and it was defined as a coated composite porous membrane. Thereafter, a leukocyte removal filter device was produced in the same manner as in Example 6 with the exception that a slice of the above coated composite porous membrane was used as a second filter.

In this case also, the filling density of the entire filter element was 0.23 g/cm$^3$. Thus, the volume of the filter element was 12 cm$^3$ (the first filter+two slices of supporting membranes).

Thereafter, 450 cm$^3$ of fresh human whole blood was passed through this integral-type leukocyte removal filter device, so as to measure the capability of removing leukocytes thereof. A blood filtration experiment was carried out twice. As a result the mean value of the capability of removing leukocytes was found to be 4.5.

These results are shown in Table 2.

Comparative Example 5

32 slices of square non-woven fabric samples were cut out of the non-woven fabric coated with a HEMA/DMAMA (97/3 (molar ratio)) copolymer obtained in section 1-2 of Example 1, such that the effective filter area could be 45 cm$^2$ (effective filter size: 6.7 cm×6.7 cm). Such 32 slices were filled into a filter holder, so as to constitute a leukocyte removal filter device (filling density: 0.23 g/cm$^3$). A composite porous membrane (that is, a second filter) was not used herein. The volume of a filter element was 24 cm$^3$, and the effective filter area was 45 cm$^2$.

Thereafter, a leukocyte filtration experiment was carried out twice. That is, 450 cm$^3$ of fresh human whole blood was passed through this leukocyte removal filter device twice. As a result, the mean value of the capability of removing leukocytes was found to be 4.2.

The results are shown in Table 2. This device exhibited high capability of removing leukocytes, but the volume of a filter element was twice larger than that of Example 5.

Comparative Example 6

An integral-type leukocyte removal device was produced in the same manner as in Example 5 with the exceptions that a first filter was constituted with 3 slices of coated non-woven fabrics and that a second filter was constituted with 2 slices of coated composite porous membranes.

The capability of the first filter of removing leukocytes was 0.5. The volume of filter element (the first filter+the supporting membrane of the composite porous membrane) of the finally constructed integral-type leukocyte removal filter device was 2 cm$^3$.

Thereafter, in order to measure the capability of this integral-type leukocyte removal filter device of removing leukocytes, 450 cm$^3$ of fresh human whole blood was passed through the above device. However, since the filter was occluded due to clogging during the filtration, such evaluation ended up unsuccessfully.

It was found that when the capability of the first filter of removing leukocytes was insufficient, the clogging of the filter occurs unfavorably.

Example 8

1. Production of Cup-Type Culture Apparatus by Processing of Composite Porous Membrane The composite porous membrane produced in Example 3 was cut into a round shape of 13 mmφ. Using a chloroform solution containing PSU with a polymer concentration of 17% as an adhesive agent, the porous membrane face of the cut round composite porous membrane was attached to one end face of a glass ring (manufactured by Asahi Technoglass Corp.; Cloning Ring; inside diameter: 10 mm, outside diameter: 12 mm, and height: 10 mm), so as to produce a cup-type culture apparatus. This cup-type culture apparatus was subjected to air drying and then to vacuum drying. The resultant culture apparatus was treated with an autoclave at 121° C. for 10 minutes, so as to sterilize it.

The thus autoclave-treated cup-type culture apparatus was immersed in an aqueous 0.3% type I collagen solution (CELLGENI-PC, manufactured by Koken Co., Ltd.), followed by air drying, thereby obtaining a collagen-coated cup-type culture apparatus.

2. Cell Culture

2-1. Introduction of Cells into Supporting Porous Membrane

Using a different diameter adaptor, one end of a silicon tube with an inside diameter of 12 mm and an outside diameter of 14 mm was connected with an opening of a 10-ml disposable syringe (manufactured by Terumo Corp). The other end thereof was connected with a glass ring portion of the cup-type culture apparatus coated with collagen in the aforementioned section 1.

Human cervical adenocarcinoma cells (ATCC No. CCL-2) were used as model cells. Such cells were added to a cell culture solution (D-MEM, manufactured by GIBCO), resulting in 1×10$^4$ cells/100 μL, so as to prepare a cell suspension.

The cup-type culture apparatus was placed with the supporting porous membrane of a composite porous membrane located upward, and 100 μL of the prepared cell suspension was then added dropwise to the supporting porous membrane, followed by aspiration with the disposable syringe. Thereafter, 5 ml of a culture solution was further added dropwise thereto, followed by aspiration, so as to introduce cells. In a state where the supporting porous membrane was located upward, the resultant was left under aseptic conditions for 30 minutes. The number of cells contained in the recovered cell culture solution that had been passed through the composite porous membrane and then poured into the syringe was intended to be counted under a phase-contrast optical microscope using a hemacytometer (EOSINOPHIL COUNTER, manufactured by Sun Lead Glass). However, the presence of cells could not be confirmed.

2-2. Cell Culture

Thirty minutes later, while maintaining the state where the supporting porous membrane was located upward, it was placed in a well of a 24-well polystyrene culture plate (Multiwell™ Cell Culture Plate, manufactured by BD Bioscience, U.S.A.). Thereafter, 2 ml of a culture solution was added thereto, such that even the upper portion of the membrane was immersed in the culture solution. This culture plate was left at rest in a moisture-retentive incubator at 37° C. in the presence of 5% $CO_2$ in an atmosphere of 95% air, and it was cultured for 2 days.

Two days later, the cup-type culture apparatus was removed, and 5 ml of a 0.05% trypsin solution was passed through it. Thereafter, 10 ml of a culture solution was further passed through it, and cells in the supporting porous membrane were then recovered. The number of cells in the recovered solution was counted under a phase-contrast optical microscope using a hemacytometer. As a result, it was found that the number of cells 3-times increased.

Likewise, after completion of the culture, the cup-type culture apparatus was removed from the well, and the cells were then fixed with an aqueous 2% glutaraldehyde solution. Thereafter, the composite porous membrane was cut out of the cup-type culture apparatus.

The section of the cut composite porous membrane was observed under a scanning electron microscope, so as to examine the distribution of cells in the supporting porous membrane. As a result, it was found that the cells were present on the periphery of the porous membrane, and that the cells were also present in other portions of the supporting porous membrane.

Moreover, when compared with comparative example 7, the number of grown cells was large. It was found that since the area acting as a scaffolding for cells increased due to the presence of the supporting porous membrane, the cells could efficiently be cultured.

From these results, it was found that it is possible to introduce cells into the supporting porous membrane up to the periphery of the porous membrane, and that the cells is able to grow in the supporting porous membrane. That is to say, if difference types of cells are inoculated on the porous membrane in the aforementioned state, the different types of cells are allowed to efficiently come into contact with each other through the porous membrane. Moreover, it is anticipated that the cells introduced into the supporting porous membrane up to the periphery of the porous membrane can be cultured without a decrease in the cell activity, because of interaction with other cells in the supporting porous membrane.

Comparative Example 7

Using an etched membrane made from polycarbonate (PC) (Isopore Membrane Filter, manufactured by MILLIPORE), a cup-type culture apparatus was produced in the same manner as in the sectional of Example 8. The culture apparatus was sterilized and then subjected to collagen coating.

Human cervical adenocarcinoma cells (ATCC No. CCL-2) were used as model cells. Such cells were added to a cell culture solution (D-MEM, manufactured by GIBCO), resulting in $1\times10^4$ cells/100 µL, so as to prepare a cell suspension. The cup-type culture apparatus was placed with the etched membrane side located upward, and 100 µL of the prepared cell suspension was then added dropwise to the etched membrane, and the cup-type culture apparatus was left for 30 minutes under antiseptic conditions in the state where the etched membrane was located upward. During such a process, the culture solution was likely to pass through the etched membrane and be then poured into the cup, and the membrane face was thereby easily be dried. Thus, a IId was put thereon, so as to prevent drying. Moreover, a small amount of culture solution should be added as necessary, thereby causing extremely poor operability.

Thereafter, culture was carried out for 2 days in the same manner as in the section 2-2 of Example 8, and cells were then recovered using a trypsin solution. Thereafter, the number of the cells was counted. As a result, the number of the cells 2-times increased.

Example 9

Human cervical adenocarcinoma cells were introduced into the collagen coated cup-type culture apparatus produced in the same manner as in the section 1 of Example 8, at an amount of $1\times10^4$ cells/100 µl in the same manner as in section 2-1 of Example 8.

Thirty minutes after the introduction, the cup-type culture apparatus was placed in a well of a 24-well polystyrene culture plate, with the supporting porous membrane located downward. Thereafter, 1 ml of a culture solution was added thereto, and culture was then carried out in an incubator for 2 days.

Two days later, cells were then recovered using a trypsin solution in the same manner as in Example 8. Thereafter, the number of the cells was counted. As a result, it was found that the number of the cells 2.8-times increased.

When compared with Comparative example 8, even when the cup-type culture apparatus was turned over, since the supporting porous membrane acted as a scaffolding for cells, the cells were not easily removed, but they were retained in the composite porous membrane. Thus, the number of the recovered cells was large. From such results, it was found that it is extremely easy to continuously inoculate the second cells on the porous membrane.

Comparative Example 8

Using an etched membrane made from polycarbonate (PC) (Isopore Membrane Filter, manufactured by MILLIPORE), a collagen-coated cup-type culture apparatus was produced in the same manner as in Comparative example 7. Thereafter, the etched membrane side was disposed upward, and 100 µl of a cell suspension containing human cervical adenocarcinoma cells at an amount of $1\times10^4$ cells/100 µl was then added dropwise on the etched membrane. Thereafter, the cup-type culture apparatus was left for 30 minutes under antiseptic conditions in the state where the etched membrane was located upward, while paying attention to prevent the membrane from being dried.

Thirty minutes after addition of the cell suspension, the cup-type culture apparatus was placed in a well of a 24-well polystyrene culture plate, with the etched membrane portion located downward. Thereafter, 1 ml of a culture solution was added thereto, and culture was then carried out in an incubator for 2 days.

Two days later, cells adhering to the etched membrane were then recovered using a trypsin solution in the same manner as in Example 8, and the number of the cells was then counted. As a result, it was found that the number of the cells decreased to 0.5-times. It was considered that when the etched membrane was placed in a well, many cells were removed.

TABLE 1

| | Production conditions | | | | Composite porous membrane | | | | |
| | Hydrophobic organic solvent solution | | | | | Porous membrane | | | |
| | | | | | | | Average | | Percentage | Average |
| | Hydrophobic organic solvent | Polymer concentration (g/L) | Liquid amount (m/L) | Supporting porous membrane | Material | Opening ratio (%) | pore diameter D (µm) | σd/D | of through-pores (%) | membrane thickness T (µm) |
|---|---|---|---|---|---|---|---|---|---|---|
| Example 1 | Chloroform | 1 | 14 | PET non-woven fabric (hydrous) | PCL | 48 | 4.0 | 0.28 | 87 | 2.3 |
| Example 2 | Dichloromethane | 1 | 14 | PET non-woven fabric (hydrous) | PCL | 51 | 3.3 | 0.18 | 82 | 1.5 |
| Example 3 | Chloroform | 1 | 14 | PET non-woven fabric (hydrous) | PSU | 54 | 3.2 | 0.19 | 85 | 2.9 |
| Example 4 | Chloroform | 4 | 21 | PET non-woven fabric (hydrous) | PSU | 35 | 6.8 | 0.15 | 72 | 6.5 |
| Comparative Example 1 | Chloroform | 1 | 11 | Non | PCL | 50 | 5.1 | 0.16 | 81 | 2.5 |
| Comparative Example 2 | Chloroform | 4 | 21 | Non | PSU | 38 | 7.0 | 0.14 | 68 | 5.9 |

TABLE 1-continued

| | | | | | | | | | | |
|---|---|---|---|---|---|---|---|---|---|---|
| Comparative Example 3 | Chloroform | 4 | 17 | PET non-woven fabric (dried) | PSU | Smooth porous membrane could not be formed | | | | |
| Comparative Example 4 | Etched membrane | | | | PC | 8 | 5.0 | 0.08 | (100) | 20 |

| | | Composite porous membrane Porous membrane | | test | | | |
|---|---|---|---|---|---|---|---|
| | | σt/T | Internal structure | Supporting porous membrane Material | Simple tensile test | adhesion test | Simple water permeability test (ml/cm²/min) | Time required for permeation of 2 ml of hemocyte suspension (second) |
| Example 1 | 0.25 | Spherical through-pore | PET | ○ | ○ | 17.6 | 30 |
| Example 2 | 0.23 | Spherical through-pore | PET | ○ | ○ | 15.4 | — |
| Example 3 | 0.35 | Spherical through-pore | PET | ○ | ○ | 14.2 | — |
| Example 4 | 0.27 | Spherical through-pore | PET | ○ | ○ | 19.6 | — |
| Comparative Example 1 | 0.15 | Spherical through-pore | Non | X | X | 18.9 | — |
| Comparative Example 2 | 0.20 | Spherical through-pore | Non | X | X | 20.1 | — |
| Comparative Example 3 | | Smooth porus membrane could not be formed | PET | — | — | — | — |
| Comparative Example 4 | 0.10 | Cylindrical through-pore | Non | ○ | — | 12.0 | 57 |

TABLE 2

| | Amount of hemocyte suspension to be treated (cm³) | First filter (non-woven fabric) | | |
|---|---|---|---|---|
| | | Effective area (cm²) | Number of non-woven fabric (slice) | Capability of removing leukocytes |
| Example 5 | 450 | 45 | 16 | 2.8 |
| Example 6 | 450 | 45 | 15 | 2.7 |
| Example 7 | 450 | 45 | 16 | 2.8 |
| Comparative Example 5 | 450 | 45 | 32 | 4.2 |
| Comparative Example 6 | 450 | 45 | 3 | 0.5 |

| Second filter (Composite porous membrane) | | | | | | | | | | Leukocyte removal filter device | |
|---|---|---|---|---|---|---|---|---|---|---|---|
| Number of Composite porous Membranes (slice) | Effective area (cm²) | Porous membrane | | | | | | | Supporting porous membrane Material | Volume of filter element (cm³) | Capability of removing leukocytes |
| | | Material | Opening ratio (%) | D (μm) | σd/D | Percentage of through-pores (%) | Membrane thickness (μm) | σt/T | Internal structure | | |
| 1 | 45 | PCL | 48 | 4.0 | 0.28 | 87 | 2.3 | 0.25 | Spherical through-pore | PET non-woven fabric | 12 | 4.3 |
| 2 | 45 | PCL | 48 | 4.0 | 0.28 | 87 | 2.3 | 0.25 | Spherical through-pore | PET non-woven fabric | 12 | 4.5 |

TABLE 2-continued

| | | | | | | | | | | | | |
|---|---|---|---|---|---|---|---|---|---|---|---|---|
| 1 | 45 | PCL | 51 | 3.3 | 0.18 | 82 | 1.5 | 0.23 | Spherical through-pore | PET non-woven fabric | 12 | 4.5 |
| 0 | — | — | — | — | — | — | — | — | — | — | 24 | 4.2 |
| 2 | 45 | PCL | 48 | 4.0 | 0.28 | 87 | 2.3 | 0.25 | Spherical through-pore | PET non-woven fabric | 3.5 | Occluded |

INDUSTRIAL APPLICABILITY

The composite porous membrane of the present invention has a pore size of μm order, high uniformity, and high opening ratio. In addition, the present composite porous membrane adopts a structure whereby the inside of the membrane has high filtration efficiency, and a supporting membrane thereof has sufficient mechanical strength. Accordingly, the composite porous membrane of the present invention can be widely used as a main filter, pre-filter, or final filter for filtration (separation and recovery) of target substances of μm order, such as various types of cells, bacteria or yeasts, and further for the purpose that requires precise size separation of μm order.

Specifically, the present composite porous membrane can be effectively used as a cell separation filter for batch processing or circle processing in a bioprocess field for producing value-added pharmaceutical products, food products, nutrient preparations, and others.

In a medical field, the composite porous membrane of the present invention can be used as a leukocyte removal filter for whole blood, an erythrocyte product, a thrombocyte product, a plasma product, etc. It may be used either singly or with the combination of the conventional filter element.

When the present composite porous membrane is used singly, since it has high strength, it can be used as a thin-type leukocyte removal filter having no risks of membrane break due to high filtration pressure.

The present composite porous membrane can be used as a cell separation filter for various types of blood cells, such as separation of erythrocytes, leukocytes, or thrombocytes. Moreover, it can also be used as a plasma separation filter from whole blood.

According to the present invention, when leukocytes are removed, the volume of a filter element can be significantly reduced while maintaining high capability of removing leukocytes. Thus, it becomes possible to significantly reduce the loss of a hemocyte suspension (whole blood, an erythrocyte product, a thrombocyte product, a plasma product, etc.) caused by the volume of filter element during filtration. As a result, the present invention brings on various effects such that cost performance regarding blood products can be significantly improved in medical sites, that the cost generated on the filter production side can be reduced due to reduction in the amount of a filter constitutional material, and that such a thin-type product enables the efficiency of storage space or the improvement of the workability of users in medical sites.

When an electrolyte solution, an agent, or a nutrient preparation is intravenously administered in a parenteral manner, the composite porous membrane of the present invention can also be used as an IV filter for removing foreign matters mixed (bacteria or microparticle substances), a leukocytic cell-recovering filter for recovering leukocytic cells from a hematopoietic stem cell source such as peripheral blood, cord blood or bone marrow, a monocyte-recovering filter, a hematopoietic stem cell-recovering filter, or a cell separation filter used in the regenerative medicine field of various organs.

The cell culture diaphragm of the present invention is effectively used as a cell culture diaphragm, when the growth of useful cells of interest is controlled by intracellular contact with different cells (for example, when the cells of interest are allowed to grow while suppressing its differentiation), and also when only such useful cells intend to be selectively recovered after the growth. In particular, since there is a possibility that undifferentiated hematopoietic stem cells are allowed to grow in high volume using this cell culture diaphragm, it is anticipated that the present cell culture diaphragm be extremely effectively used in a regenerative medicine field or transfusion field (clean transfusion using cultured blood cells). Moreover, it is also anticipated that the present cell culture diaphragm be used also in a regenerative medicine/cell therapy field involving the growth of organ-specific stem cells.

Furthermore, the composite porous membrane of the present invention can be used as a uniformly dispersed medium for ink or the like in an electronic material field such as a master in silk-screen printing.

The invention claimed is:

1. A process for co-culturing cells of a first cell group and cells of a second cell group while partitioning the first and second cell groups by a cell culture diaphragm in a cell culture solution so that the cells of the two kinds of cell groups can come into contact with each other, said cell culture diaphragm comprising a composite porous membrane which comprises at least one porous membrane comprising an organic polymer and at least one supporting porous membrane adjacent thereto, the supporting porous membrane having continuous pores with an average pore diameter between 1 and 100 μm, and a density of 0.1 to 0.5 g/cm$^3$, wherein, when a membrane flat surface of the porous membrane is observed using a photomicrograph, the porous membrane has an opening ratio between 10% and 90%, an average pore diameter D (μm) of $0.1 \leq D \leq 50$, a standard deviation σd (μm) of pore diameter of $0 \leq \sigma d/D \leq 0.6$, and the percentage of through-pores to all the pores of the porous membrane is 30% or more; and when a membrane section thereof is observed using a photomicrograph, the porous membrane has an average membrane thickness T (μm) defined by $0.05 \leq T/D \leq 2$ and a structure in which pores adjacent to one another communicate with one another therein;

the process comprising:

inoculating the cells of the first cell group on the side of the supporting porous membrane, inoculating the cells of the second cell group on the side of the porous membrane, and co-culturing the cells of the first and second cell groups while laying the side of the porous membrane up.

2. The method according to claim 1, wherein the porous membrane has an opening ratio between 15% and 80% and an average pore diameter D (μm) of $0.5 \leq D \leq 20$.

3. The method according to claim 1, wherein the porous membrane has an average membrane thickness T (μm) of $0.1 \leq T \leq 50$.

4. The method according to claim 1, wherein the porous membrane has an average pore diameter D (μm) of $0.1 \leq D \leq 20$ and an average membrane thickness T (μm) of $0.1 \leq T \leq 20$, and wherein a standard deviation σt (μm) of the membrane thickness is defined by $0 \leq \sigma t/T \leq 0.5$.

5. The method according to claim 4, wherein the composite porous membrane further comprises a nonwoven fabric adjacent to the porous membrane, and the nonwoven fabric has an average pore diameter between 1 and 100 μm.

* * * * *